US011980739B2

(12) United States Patent
Pizzochero et al.

(10) Patent No.: US 11,980,739 B2
(45) Date of Patent: May 14, 2024

(54) DOUBLE-ACTING, TELESCOPING SCREW-DRIVEN PUMP MECHANISM DISPOSED EXTERNALLY TO RESERVOIR IN FLUID DELIVERY DEVICE

(71) Applicant: Becton, Dickinson and Company, Franklin Lakes, NJ (US)

(72) Inventors: Alessandro Pizzochero, Chelmsford, MA (US); Mark Wood, Sterling, MA (US); Muzaffer Yalgin Ozsecen, Groton, MA (US); Timothy Blum, Columbus, OH (US); Eric Hassenpflug, Westerville, OH (US); Cory Baker, Westerville, OH (US); Jeffrey Held, Columbus, OH (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 267 days.

(21) Appl. No.: 17/401,871

(22) Filed: Aug. 13, 2021

(65) Prior Publication Data
US 2022/0054739 A1    Feb. 24, 2022

Related U.S. Application Data

(60) Provisional application No. 63/066,832, filed on Aug. 18, 2020.

(51) Int. Cl.
*A61M 5/145*    (2006.01)
*A61M 5/142*    (2006.01)

(52) U.S. Cl.
CPC ...... *A61M 5/1452* (2013.01); *A61M 5/14236* (2013.01); *A61M 5/14248* (2013.01)

(58) Field of Classification Search
CPC .............. A61M 5/1452; A61M 5/3129; A61M 5/31511; A61M 5/31528; A61M 5/31535; F16H 2025/2059; F16H 25/2056; F04B 9/02
See application file for complete search history.

(56) References Cited

U.S. PATENT DOCUMENTS

| | | | |
|---|---|---|---|
| 5,097,122 A | 3/1992 | Colman et al. | |
| 5,919,167 A | 6/1999 | Mulhauser et al. | |
| 6,248,093 B1 | 6/2001 | Moberg | |
| 6,663,602 B2 | 12/2003 | Moller | |

(Continued)

FOREIGN PATENT DOCUMENTS

EP    3403680 A1    11/2018

*Primary Examiner* — James D Ponton
(74) *Attorney, Agent, or Firm* — Dickinson Wright PLLC

(57) ABSTRACT

A fluid delivery device has a syringe barrel-type reservoir with plunger, and plunger driver assembly comprising double-acting, telescoping lead screws that is located behind and outside of the barrel. Simultaneously and counter-rotating sleeve screw and center screw telescope out of a nested configuration of the plunger driver assembly and into the reservoir at a rate of double their individual and equal pitch and lead parameters when the sleeve screw is rotated. A threaded nut and gear anchor disposed on an end of the barrel receive the sleeve screw and the threaded nut causes the sleeve screw to translate and rotate in response to motor operation. A distal end of the center screw can be keyed to a plunger pusher for anti-rotation constraint when the motor is imparting rotation on the threaded nut and sleeve screw.

22 Claims, 22 Drawing Sheets

(56) References Cited

U.S. PATENT DOCUMENTS

| | | |
|---|---|---|
| 6,786,890 B2 | 9/2004 | Preuthun et al. |
| 7,063,684 B2 | 6/2006 | Moberg |
| 7,066,909 B1 | 6/2006 | Peter et al. |
| 9,022,991 B1 | 5/2015 | Moellert |
| 9,345,836 B2 | 5/2016 | Cabiri et al. |
| 9,572,927 B2 | 2/2017 | Bruggemann et al. |
| 9,656,019 B2 | 5/2017 | Cabiri et al. |
| 9,987,432 B2 | 6/2018 | Cabiri et al. |
| 10,086,145 B2 | 10/2018 | Cabiri et al. |
| 10,149,943 B2 | 12/2018 | Bar-El et al. |
| 10,149,947 B2 | 12/2018 | Bayer et al. |
| 10,159,785 B2 | 12/2018 | Cabiri |
| 10,179,204 B2 | 1/2019 | Cabiri |
| 10,251,996 B2 | 4/2019 | Bente, IV et al. |
| 10,376,647 B2 | 8/2019 | Farris et al. |
| 10,420,880 B2 | 9/2019 | Degtiar et al. |
| 2004/0000818 A1 | 1/2004 | Preuthun et al. |
| 2009/0299290 A1 | 12/2009 | Moberg |
| 2011/0213329 A1* | 9/2011 | Yodfat ............ A61M 5/14248 604/154 |
| 2013/0245604 A1 | 9/2013 | Kouyoumjian et al. |
| 2014/0330206 A1* | 11/2014 | Moore ............ A61M 5/14216 604/152 |
| 2014/0364808 A1 | 12/2014 | Niklaus et al. |
| 2016/0114109 A1 | 4/2016 | Lavi |
| 2017/0112998 A1 | 4/2017 | Degtiar et al. |
| 2017/0175859 A1 | 6/2017 | Brockmeier |
| 2017/0189607 A1 | 7/2017 | Cabiri et al. |
| 2017/0246382 A1 | 8/2017 | Niklaus |
| 2017/0319788 A1 | 11/2017 | Morris et al. |
| 2018/0021521 A1 | 1/2018 | Sanchez |
| 2018/0064888 A1* | 3/2018 | Alderete, Jr. ....... A61M 5/1452 |
| 2018/0154081 A1 | 6/2018 | Bar-El et al. |
| 2018/0250476 A1 | 9/2018 | Cabiri et al. |
| 2019/0030241 A1 | 1/2019 | Cabiri et al. |
| 2019/0091399 A1 | 3/2019 | Calasso et al. |
| 2019/0105445 A1 | 4/2019 | Bar-El et al. |
| 2019/0167899 A1 | 6/2019 | Cabiri |
| 2020/0009316 A1 | 1/2020 | Cabiri et al. |
| 2020/0023121 A1 | 1/2020 | Thomas et al. |

* cited by examiner

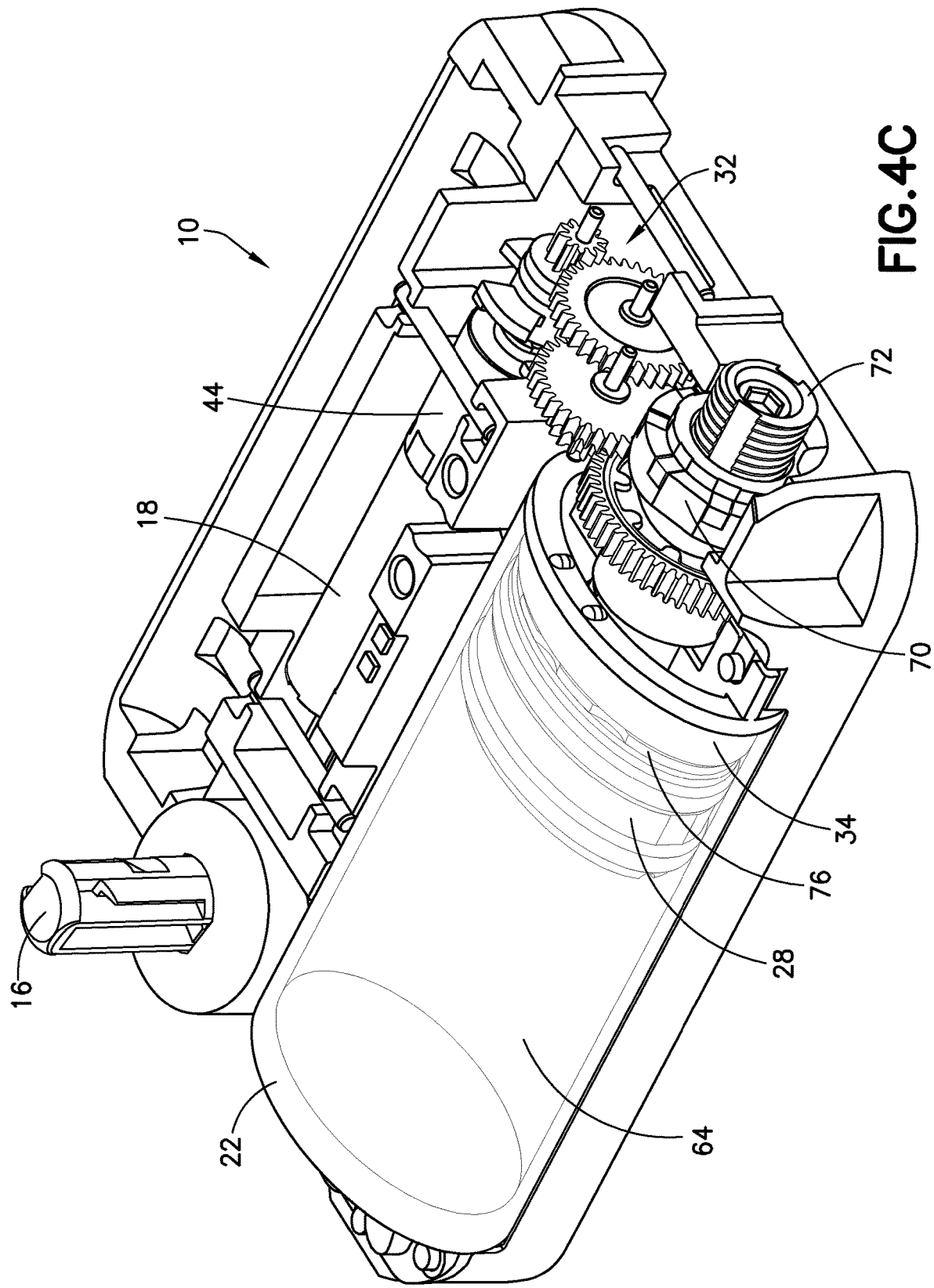

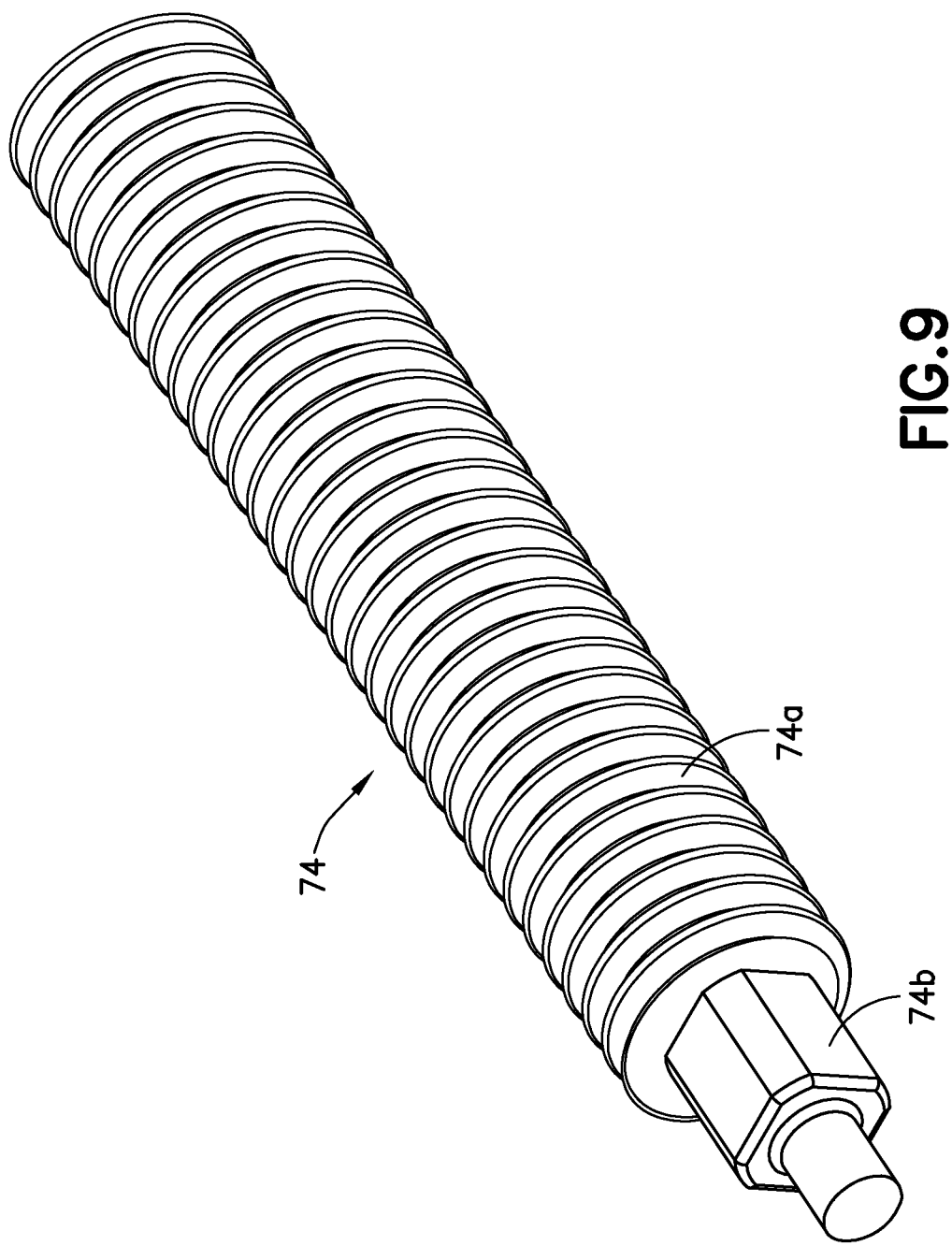

DOUBLE-ACTING, TELESCOPING SCREW-DRIVEN PUMP MECHANISM DISPOSED EXTERNALLY TO RESERVOIR IN FLUID DELIVERY DEVICE

This application claims the benefit of U.S. provisional application Ser. No. 63/066,832, filed Aug. 18, 2020, the content of which is incorporated herein by reference in its entirety.

BACKGROUND

Field

Illustrative embodiments relate generally to pump mechanisms for use in fluid delivery devices such as wearable medication infusion patches. Illustrative embodiments relate generally to screws for controllably extending or retracting a plunger driver in a syringe barrel-type reservoir that do not affect reservoir volume to ensure biocompatibility, that are fully retractable outside reservoir, and are keyed within the reservoir for anti-rotation control.

Description of Related Art

Typical drug delivery patch pump designs are challenged by the need achieve small size, low power consumption, accurate delivery, high reliability, and low manufacturing costs. In addition, drug delivery patch pump designs cannot impact drug quality. For example, the materials used for pump mechanism components that contact the delivered fluid cannot present biocompatibility problems.

SUMMARY

The above and other problems are overcome, and additional advantages are realized, by illustrative embodiments.

Example embodiments of the present disclosure realize several advantages such as minimizing the device size envelope or form factor, while retaining the beneficial features of highly reliable and proven systems such as medication pens and pen needles, syringes, or more expensive, non-portable pumping systems that employ a lead screw drive mechanism.

An aspect of illustrative embodiments is to provide an improved and novel double-acting, telescoping screw-drive pump mechanism design that enables the use of syringe barrel-type drug containers or similar reservoirs, which have been proven to be drug-friendly or biocompatible with drugs and other fluids delivered via fluid delivery devices.

In accordance with illustrative embodiments, a fluid delivery device is provided that comprises a reservoir comprising an outlet port at a distal end, and plunger movable along a longitudinal axis of the reservoir, the plunger configured to provide a seal with respect to inner walls of the reservoir to prevent fluid provided in a fluid chamber defined on a first side of the plunger and comprising the outlet port from leaking into a portion of the reservoir defined by a second side of the plunger; and a plunger driver assembly mounted at a proximal end of the reservoir and comprising telescoping, simultaneously counter-rotating screws having similar pitch and lead parameters that, when a threaded nut is rotated, move from a nested configuration that does not extend into the reservoir to an extended configuration that extends into the reservoir at a rate of double the individual pitch and lead parameters of the respective screws. In accordance with aspects of the illustrative embodiments, an encoder(s) can be provided relative to the plunger driver assembly to generate feedback data related to operation of the plunger driver assembly.

In accordance with aspects of the illustrative embodiments, the screws comprise a sleeve screw and a center screw each having opposite handed outer threads, the outer thread of the center screw being a right-hand thread if the outer thread of the sleeve screw is a left-hand thread, and the outer thread of the center screw being a left-hand thread if outer thread of the sleeve screw is a right-hand thread.

In accordance with aspects of the illustrative embodiments, the inner thread of the sleeve screw and the outer thread of the sleeve screw have opposite handed threads.

In accordance with aspects of the illustrative embodiments, the threaded nut has an aperture with inner threads that cooperate with outer threads on the sleeve screw to advance the sleeve screw into the reservoir when the threaded nut is rotated.

In accordance with aspects of the illustrative embodiments, the reservoir further comprises a gear anchor mounted to its proximal end, the gear anchor comprising an aperture dimensioned to receive a distal end of the sleeve screw and allow the sleeve screw and the center screw to extend into the reservoir when the threaded nut is rotated. In addition, the gear anchor can have a through hole for venting.

In accordance with aspects of the illustrative embodiments, the plunger driver assembly further comprises a plunger pusher member coupled to a distal end of the center screw.

In accordance with aspects of the illustrative embodiments, the plunger pusher is configured to detachably abut the plunger and push the plunger axially toward the distal end of the reservoir when the plunger driver assembly is controlled to deploy the counter-rotating screws to discharge a designated amount of fluid from the fluid chamber in the reservoir through displacement of the plunger.

In accordance with aspects of the illustrative embodiments, the center screw is connected to the plunger pusher and constrained from rotation by an anti-rotation mechanism.

In accordance with aspects of the illustrative embodiments, the anti-rotation mechanism is the reservoir and plunger pusher having a non-circular cross-section to prevent rotation of the plunger pusher within the reservoir when the sleeve screw is rotated.

In accordance with aspects of the illustrative embodiments, the plunger driver assembly further comprises an anti-rotation mechanism that comprises a detent on a proximal side of the plunger pusher dimensioned to cooperate with a distal end of the center screw to prevent the plunger pusher from rotating relative to the inner walls of the reservoir when the sleeve screw is rotated. For example, the distal end of the center or innermost screw is dimensioned and/or shaped to be pressure fit into a correspondingly dimensioned and/or shaped detent. Further, the detent can comprise a through hole to a distal side of the plunger pusher, and the distal end of the center screw can extend through the through hole, for example. The distal end of the center screw can be heat staked at the distal side of the plunger pusher at the through hole. The through hole can comprise anti-rotation slots to facilitate heat staking. Alternatively, the plunger pusher can comprise a protrusion on its distal side and the through hole can extend through the protrusion. In accordance with another aspect, the plunger pusher can comprise at least one through hole for venting, and/or indents along at least a portion of its perimeter for venting.

In accordance with aspects of the illustrative embodiments, the reservoir comprises an inlet port connected via an inlet fluid path to a fill port provided in the fluid delivery device to couple with a filling apparatus, and the plunger is configured to be displaced toward the proximal end of the reservoir as fluid is introduced into the fluid chamber from the inlet port, the plunger driver assembly being configured in its nested configuration during filling.

In accordance with aspects of the illustrative embodiments, the reservoir is a syringe barrel-type container.

In accordance with aspects of the illustrative embodiments, the reservoir and the plunger have a cross-sectional shape chosen from a non-circular shape, and an elliptical cross-section.

In accordance with aspects of the illustrative embodiments, the respective screws have equal pitch.

Additional and/or other aspects and advantages of illustrative embodiments will be set forth in the description that follows, or will be apparent from the description, or may be learned by practice of the illustrative embodiments. The illustrative embodiments may comprise apparatuses and methods for operating same having one or more of the above aspects, and/or one or more of the features and combinations thereof. The illustrative embodiments may comprise one or more of the features and/or combinations of the above aspects as recited, for example, in the attached claims.

BRIEF DESCRIPTION OF THE DRAWINGS

The above and/or other aspects and advantages of the illustrative embodiments will be more readily appreciated from the following detailed description, taken in conjunction with the accompanying drawings, of which:

FIGS. 4A, 4B, 4C and 4D are perspective top views of a fluid delivery device with the cover removed and constructed in accordance with an example embodiment and showing different stages of filling a reservoir;

FIG. 9 is a perspective view of a center screw with keying feature constructed in accordance with an example embodiment.

Throughout the drawing figures, like reference numbers will be understood to refer to like elements, features and structures.

DETAILED DESCRIPTION OF ILLUSTRATIVE EMBODIMENTS

Figure 1:
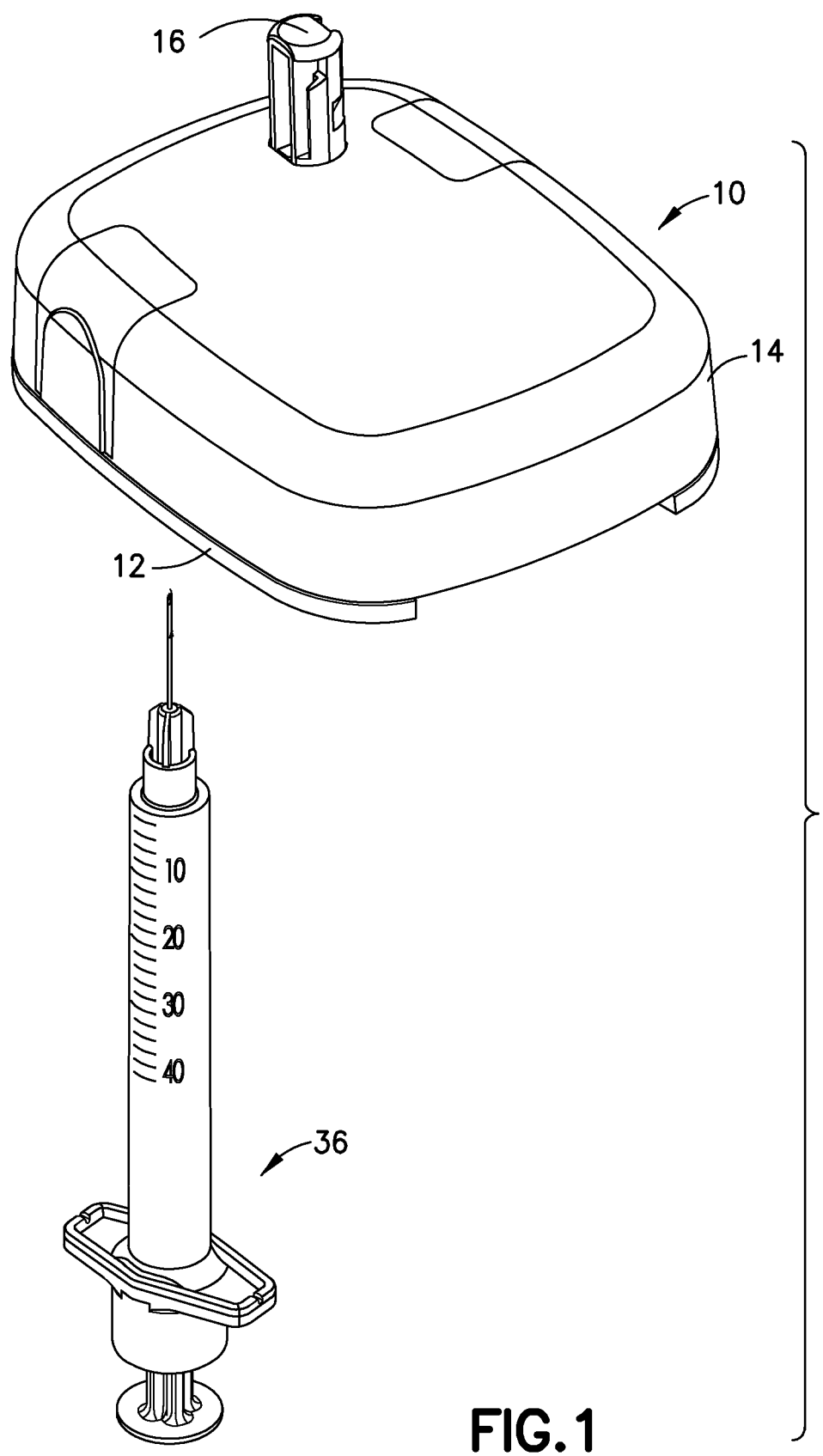
FIG. 1 is a perspective view of a wearable fluid delivery device constructed in accordance with an example embodiment.

As will be appreciated by one skilled in the art, there are numerous ways of carrying out the examples, improvements, and arrangements of a pump mechanism for a fluid delivery device in accordance with embodiments disclosed herein. Although reference will be made to the illustrative embodiments depicted in the drawings and the following descriptions, the embodiments disclosed herein are not meant to be exhaustive of the various alternative designs and embodiments that are encompassed by the disclosed technical solutions, and those skilled in the art will readily appreciate that various modifications may be made, and various combinations can be made with departing from the scope of the disclosed technical solutions.

Example embodiments of the present disclosure realize several advantages such as minimizing the device size envelope or form factor, while retaining the beneficial features of highly reliable and proven systems such as medication pens and pen needles, syringes, or more expensive, non-portable pumping systems that employ a lead screw drive mechanism. In accordance with example embodiments described herein, a novel pump mechanism for a fluid delivery device. A nesting telescopic screw design is employed for the pump mechanism that enables the use of syringe barrel-type drug containers or similar reservoirs, which have been proven to be drug-friendly or biocompatible with drugs and other fluids delivered via fluid delivery devices. A double-acting, telescoping lead screw mechanism that is located behind and outside of the syringe barrel-type reservoir. Example embodiments described herein achieve a highly precise, controllable, compact, and efficient pump design that has minimal to no impact on drug quality. In accordance with the example embodiments, telescoping, simultaneously counter-rotating sleeve screw and center screw are employed that telescope out of their nested configuration at a rate of double their individual and equal pitch/lead parameters. In order to achieve the counter-rotating functionality, the innermost screw and sleeve screw outer threads (as well as the reservoir cap threads) must be of opposite handedness. An innermost or center screw can be either left-hand or right-hand as long as the sleeve screw outer threads (and reservoir cap inner threads) are respectively right-hand or left-hand. Further, the inner threads on the sleeve screw are always of opposite handedness compared to the same screw's outer threads. A power source rotates a gear train which rotates the sleeve screw through a nut. The center screw, which is keyed to a plunger pusher and cannot rotate, advances as the threads on the sleeve screw rotate around it. The telescoping action reduces the overall footprint of the plunger drive mechanism in contrast with a single advancing lead screw used by existing patch pumps, for example. It should be noted that the overall screw drive torque is equal to the combined torque of innermost screw and sleeve screw rotation (additive, as is the overall effective lead). Also, whether the innermost screw is left-handed or right-handed is somewhat arbitrary, unless forces from the drive mechanism, motor and/or indexer have a preferential rotational direction.

FIG. 1 is a perspective view of a wearable fluid delivery device 10 constructed in accordance with an example embodiment. The fluid (e.g., drug) delivery device 10 comprises a baseplate 12, a cover 14, and an insertion mechanism 16 in an undeployed position. A reservoir fluid delivery device 10 can be filled with the fluid (e.g., drug) by a user inserting a needle of a filled syringe 36 into a fill port (not shown) provided in the baseplate 12 that has an inlet fluid path from the fill port to the reservoir. It is to be understood that the fluid delivery device 10 can be filled with a fluid (e.g., drug) using different mechanisms and methods.

FIGS. 2A, 2B, 2C and 2D are, respectively, a partial top view, a perspective view, a side view, and a top view of the fluid delivery device of FIG. 1 with the cover removed and constructed in accordance with an example embodiment. The baseplate 12 supports the insertion mechanism 16, a motor 18, a power source such as a battery 20, a control board 50, and a reservoir 22 or container for storing a fluid to be delivered to a user via an outlet fluid path 24 from an outlet port of reservoir to the insertion mechanism 16. The reservoir 22 can also have an inlet port connected via an inlet fluid path 26 to a fill port (e.g., provided in the baseplate 12). The reservoir 22 contains a plunger 28 having a stopper assembly. The proximal end of the reservoir 22 is also provided with a plunger driver assembly 30 having telescoping, simultaneously counter-rotating sleeve screw 72 and center screw 74, a gear anchor 34, a nut 70 that is rotated via a gear train 32 connected to the motor 18 and gearbox 44.

Figure 3:
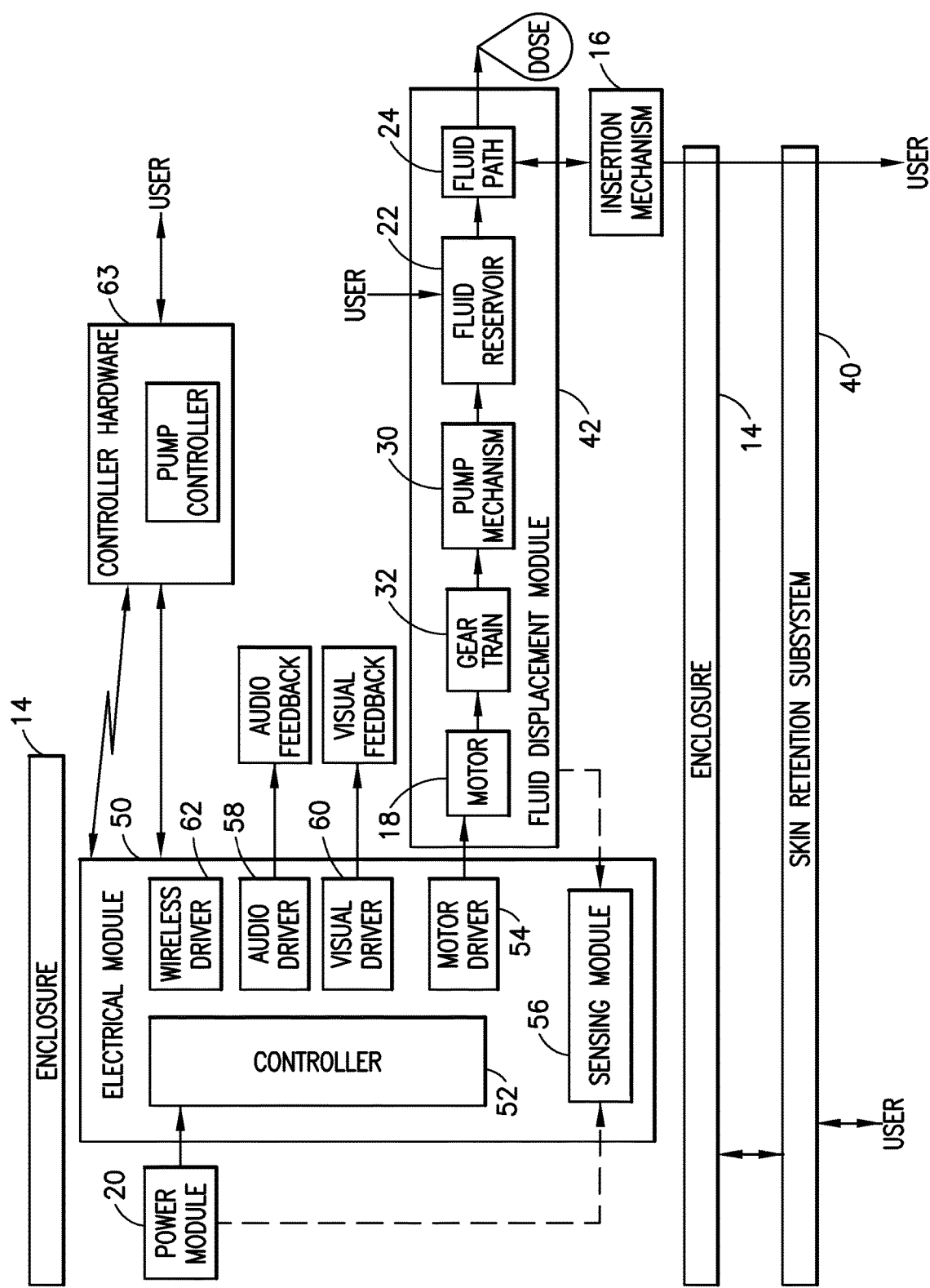
FIG. 3 is a block diagram of example components of a fluid delivery device constructed in accordance with an example embodiment.

FIG. 3 is a block diagram of example components of a fluid delivery device constructed in accordance with an example embodiment. The cover/housing or device 10 housing is indicated at 14. The device 10 has skin retention subsystem 40 such as an adhesive pad to connect the device 10 to a user's skin. The fluid delivery device 10 further comprises the reservoir 22, the insertion mechanism 16, and a fluid displacement module 42 that can include the motor 18, motor housing and gearbox 44, gear train 32, pump mechanism (e.g., plunger driver assembly 30), and outlet path 24. The fluid delivery device further comprises electrical components such as a power module (e.g., battery 20), and a electrical module 50 comprising a controller 52, a motor driver 54, optional sensing module 56 to sense fluid flow conditions (e.g. occlusion or pump mechanism runaway), optional audio driver 58 (e.g., to indicate dosing in progress, low reservoir, occlusion, successful pairing with external device, or other condition via an audible alarm such as a buzzer), and an optional visual driver 60 to provide visual feedback via a light emitting diode(s) and/or optional tactile driver to provide tactile feedback via a vibration component, and an optional wireless driver 62 for wireless communication between the fluid delivery device and an optional remote pump control device (e.g., a smartphone or dedicated controller 63). With regard to the sensing module 56, the fluid delivery device can be provided, for example, with one or more encoders to provide feedback of the drive mechanism (e.g., plunger driver assembly 30) for indexing and pump mechanism runaway prevention purposes.

FIGS. 4A, 4B, 4C and 4D are perspective top views of a fluid delivery device with the cover removed and constructed in accordance with an example embodiment and showing different stages of filling a reservoir. A fluid filled chamber 64 in the reservoir 22 is defined by a distal or front side of plunger 28 and that plunger is configured to seal the fluid from entering the portion of reservoir defined by proximal or rear side of plunger so that there is no contact with the plunger driver assembly 30 or gear anchor 34 with the fluid being delivered from the reservoir.

Figure 2A:
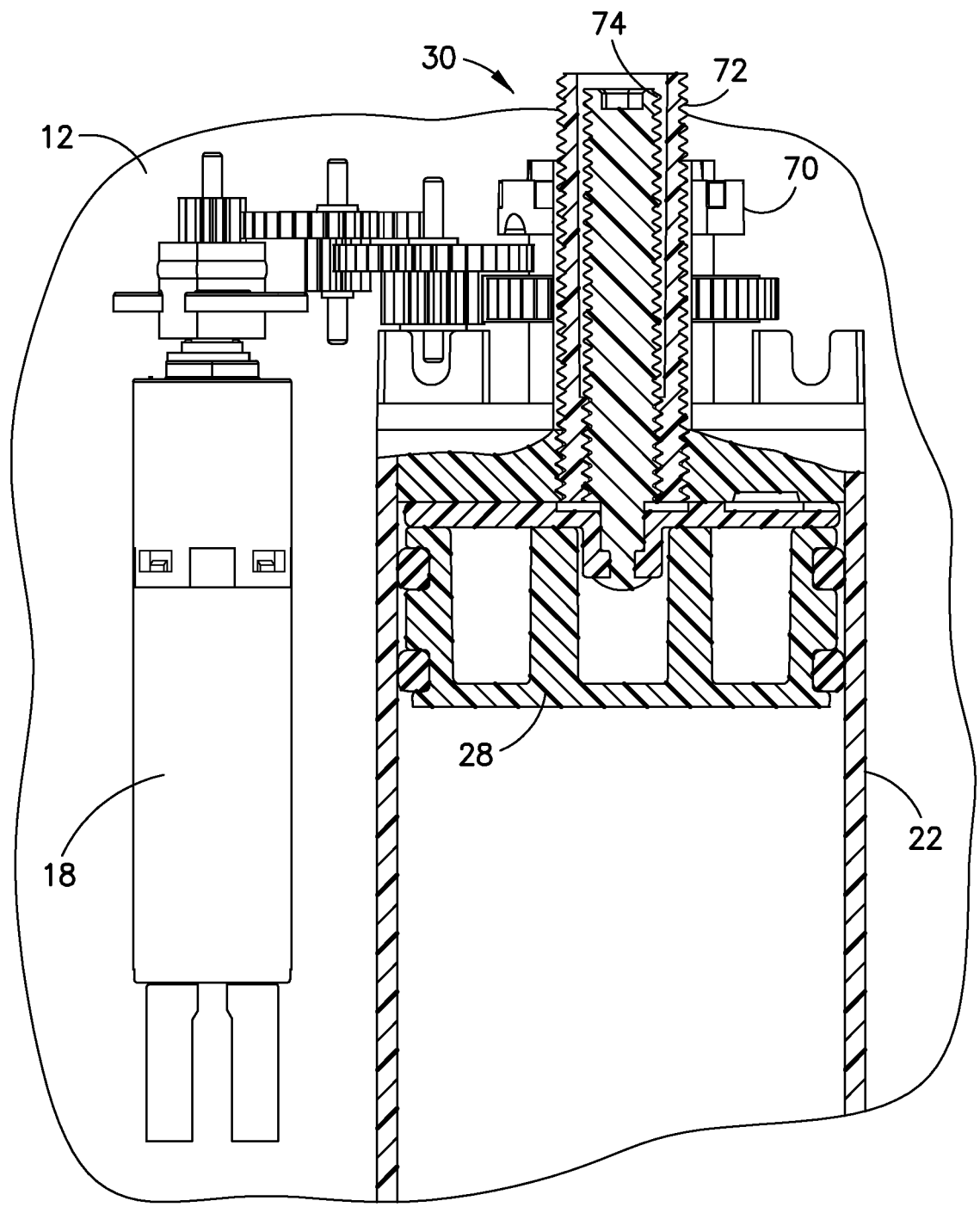
FIGS. 2A, 2B, 2C and 2D are, respectively, a partial top view, a perspective view, a side view, and a top view of the fluid delivery device of FIG. 1 with the cover removed and constructed in accordance with an example embodiment.
Figure 2B:
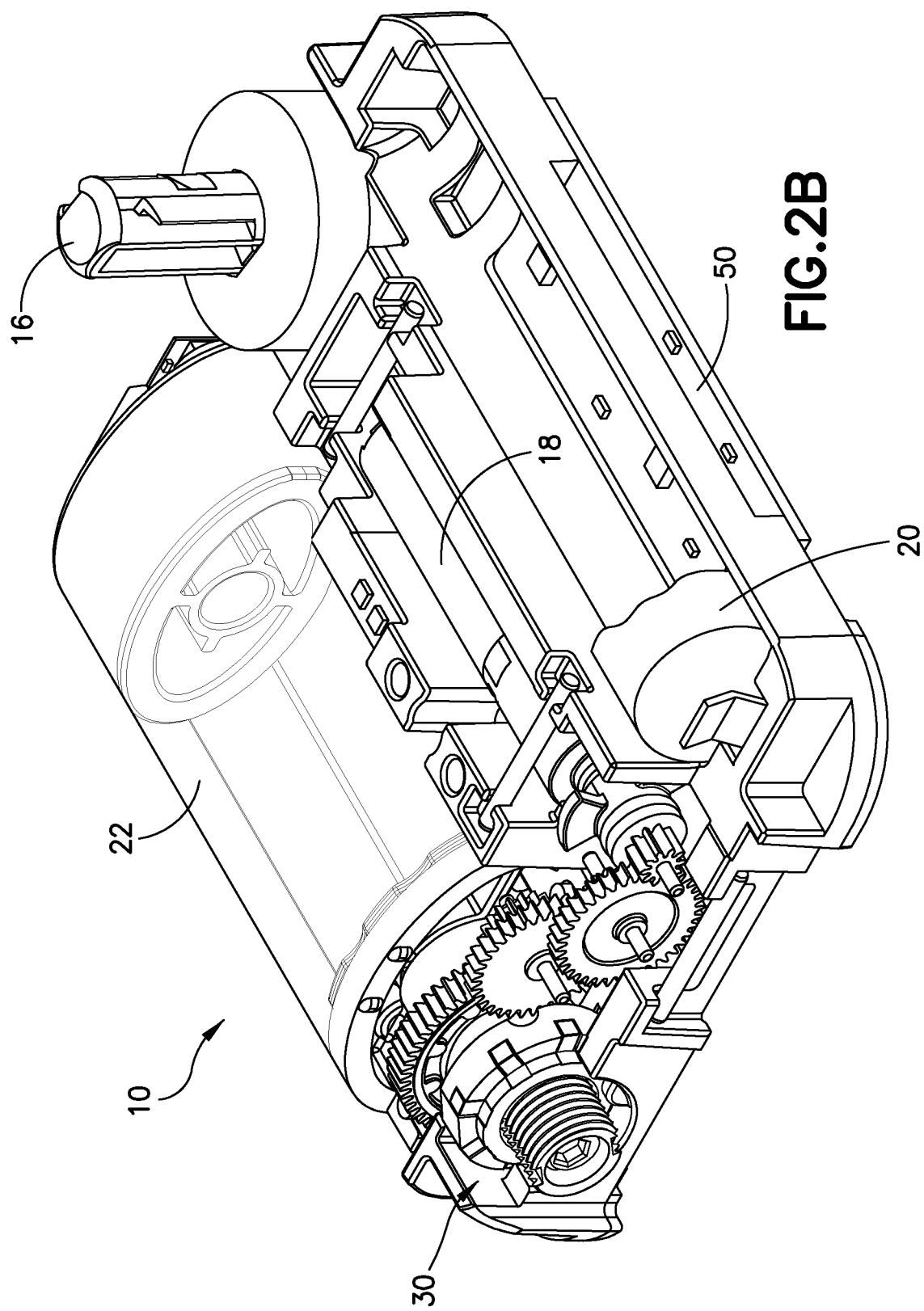
Figure 2C:
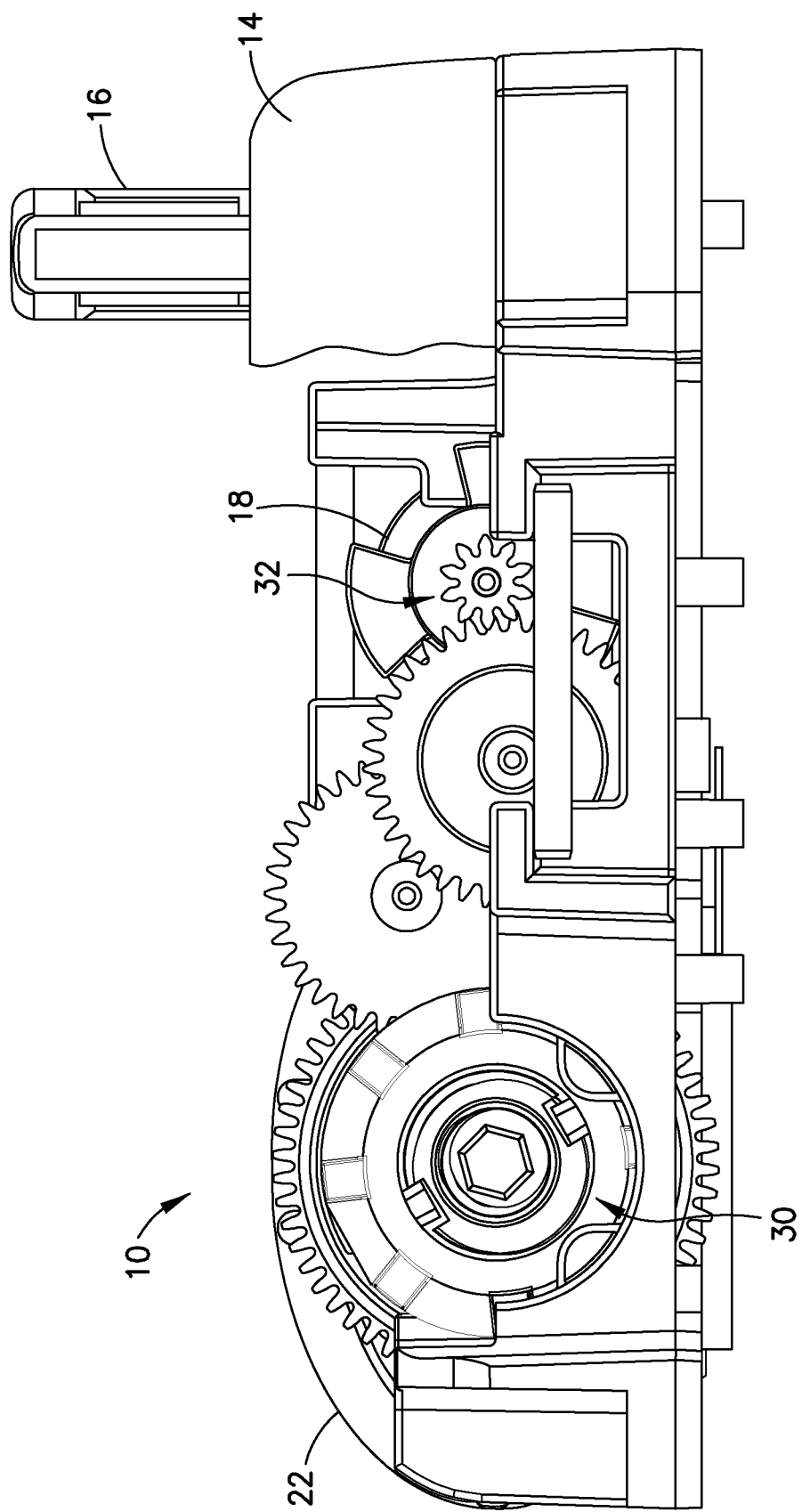
Figure 2D:
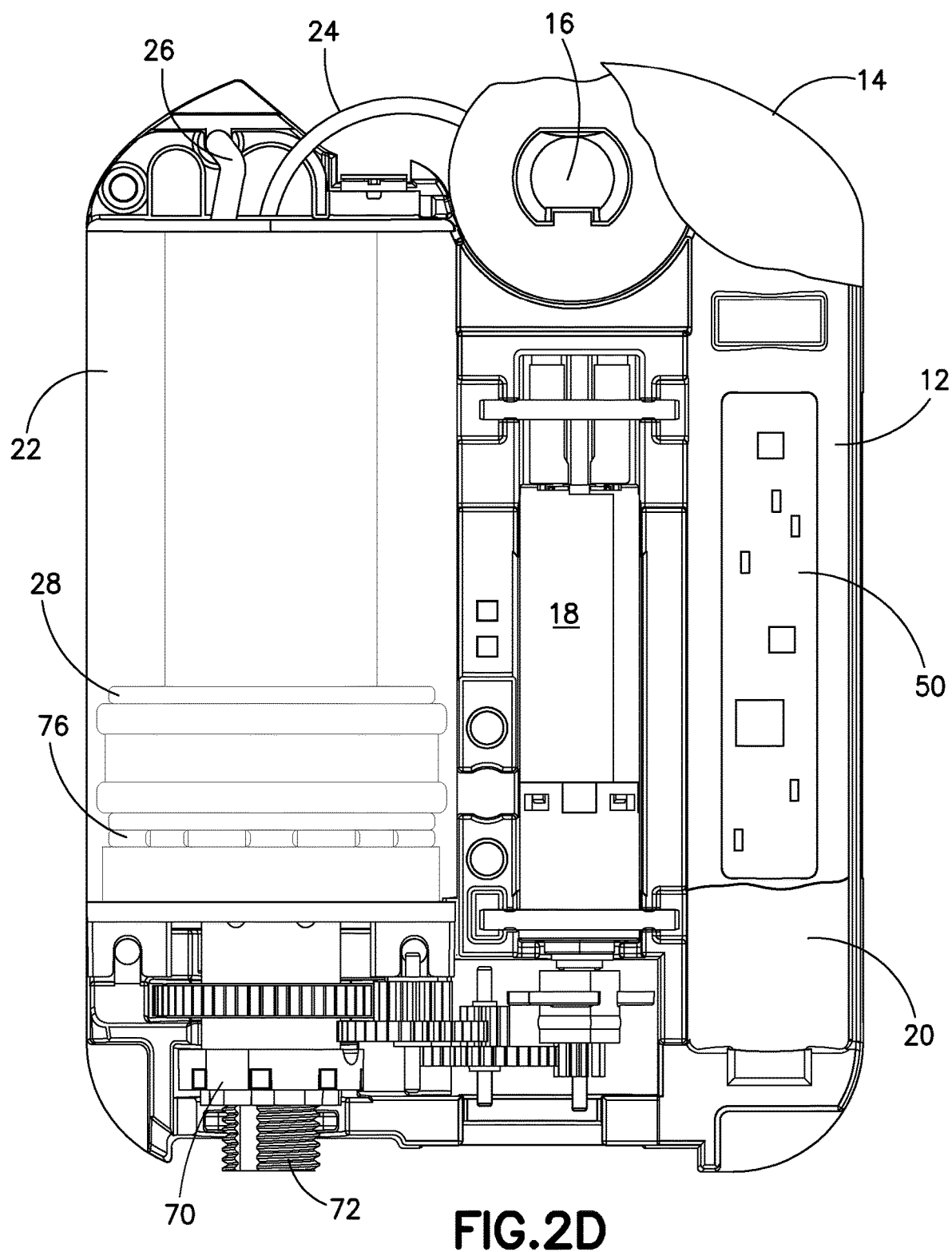
Figure 4A:
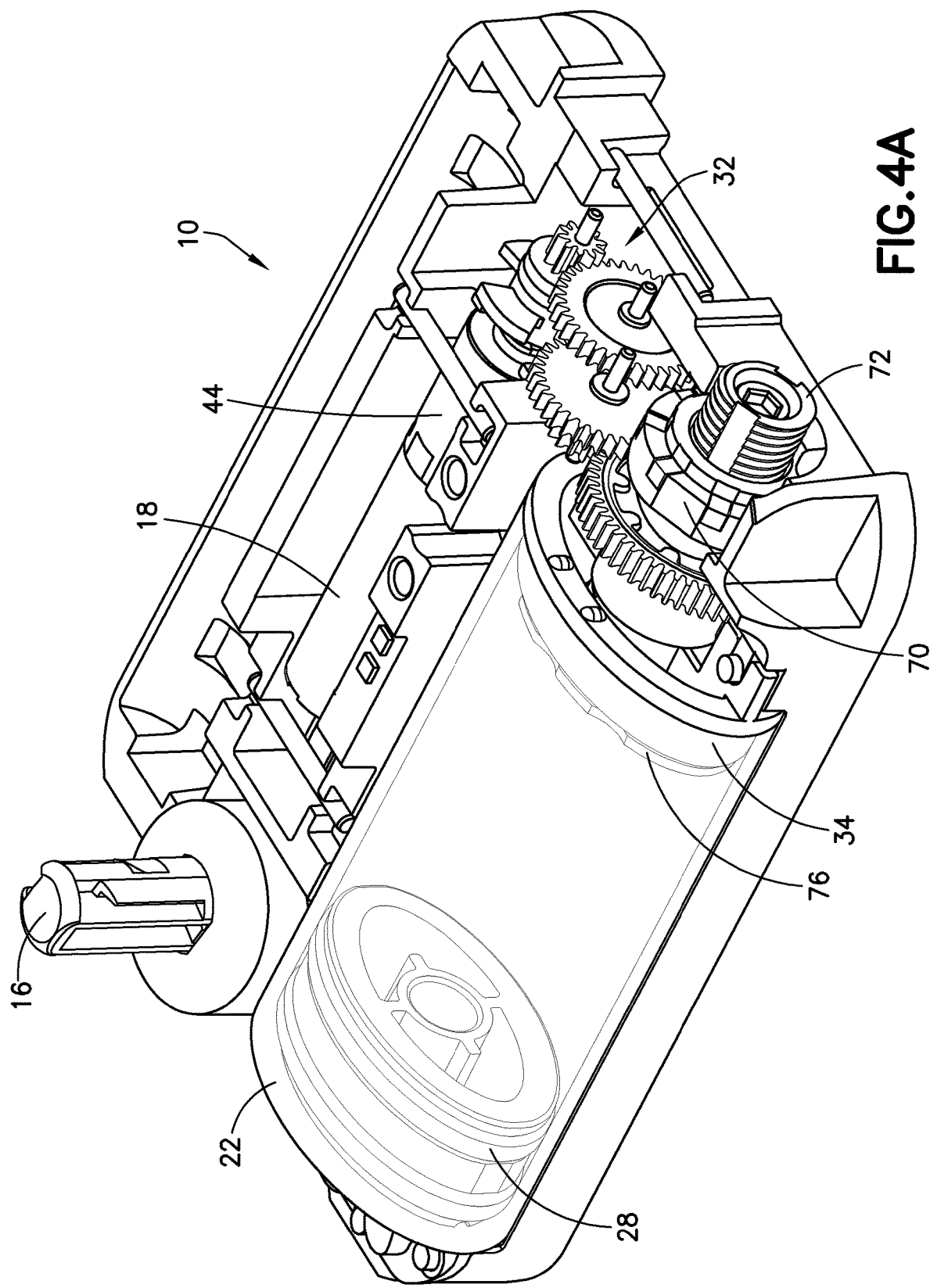
Figure 4B:
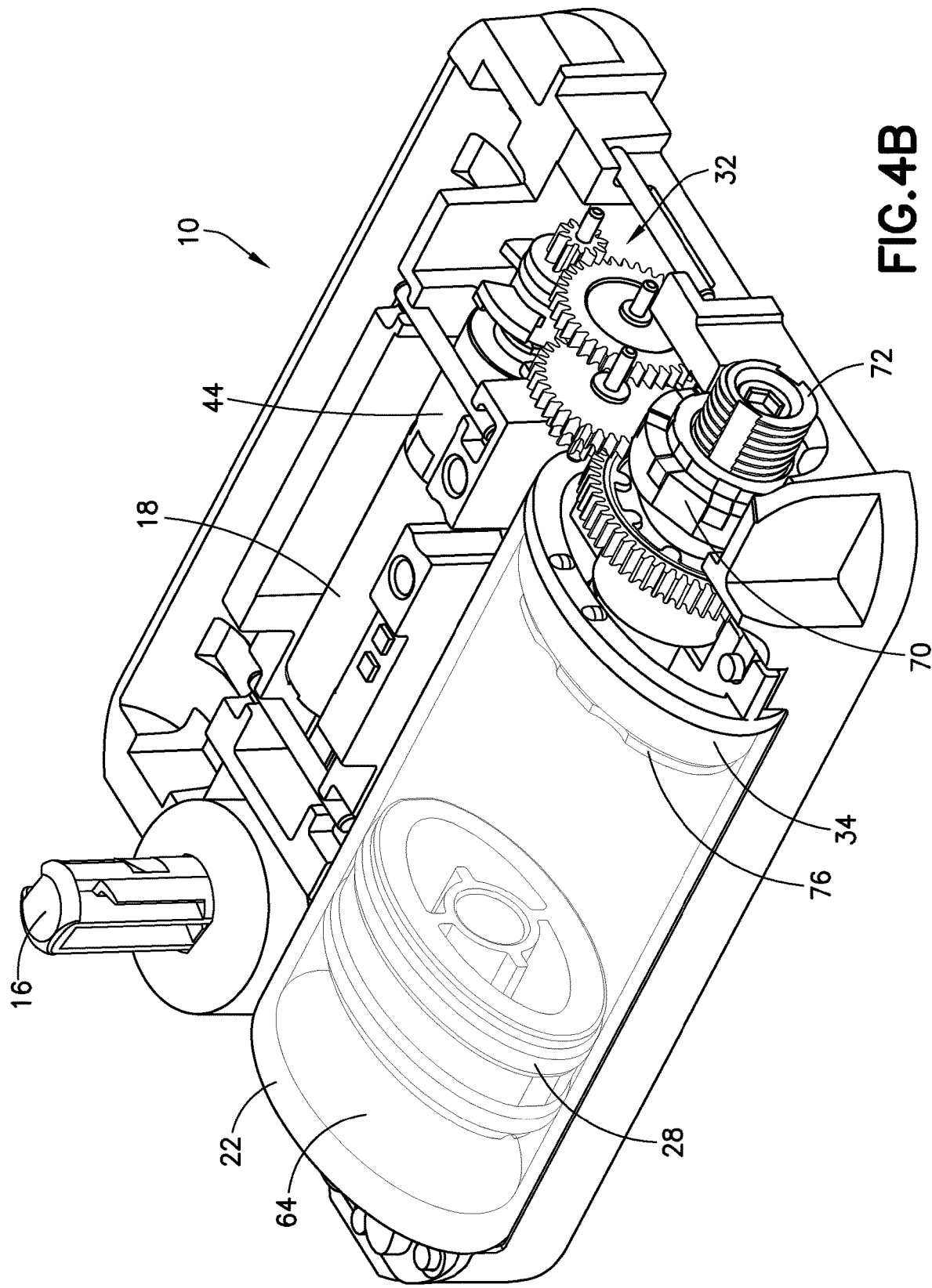
Figure 4D:
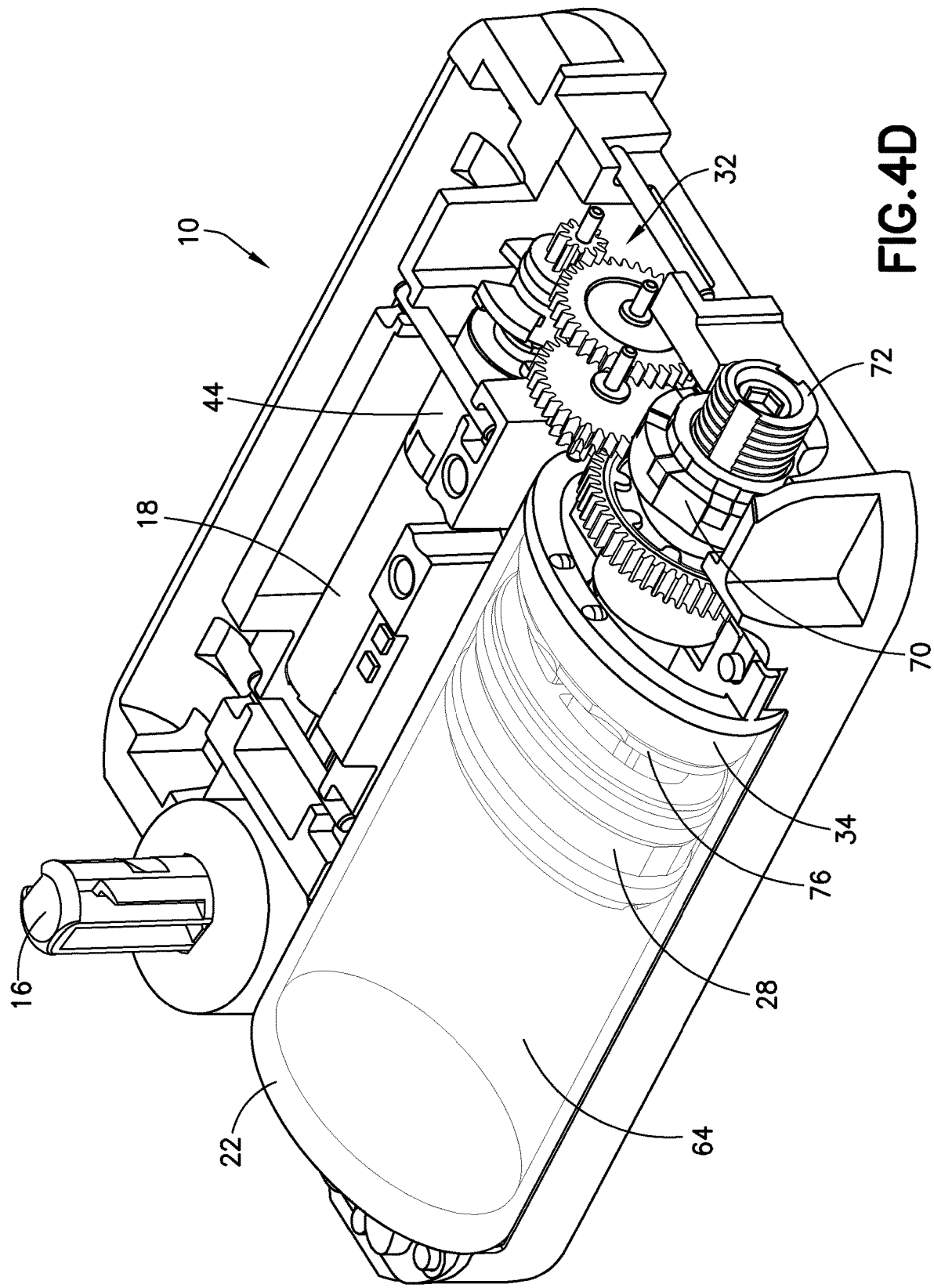

In FIG. 4A, the reservoir 22 is empty of any fluid and the plunger 28 is at its most distal position. The plunger driver assembly 30 is shown fully retracted in FIGS. 4A through 4D. A user can insert the needle of a filled syringe 36 into a fill port (not shown) provided in the baseplate 12 that has an inlet fluid path 26 from the fill port to the reservoir 22 as shown in FIG. 2D. As fluid is transferred from the syringe 36 to the reservoir 22 via the inlet fluid path 26, the volume of a fluid chamber defined in the reservoir 22 by the front surface of the plunger 28 increases, as shown in FIGS. 4B, 4C and 4D respectively. The plunger 28 has a stopper assembly to prevent leakage of any fluid retained in a fluid chamber portion 64 of the reservoir 22. The stopper assembly can comprise, for example, an elastic material similar to a syringe stopper.

Figure 5A:
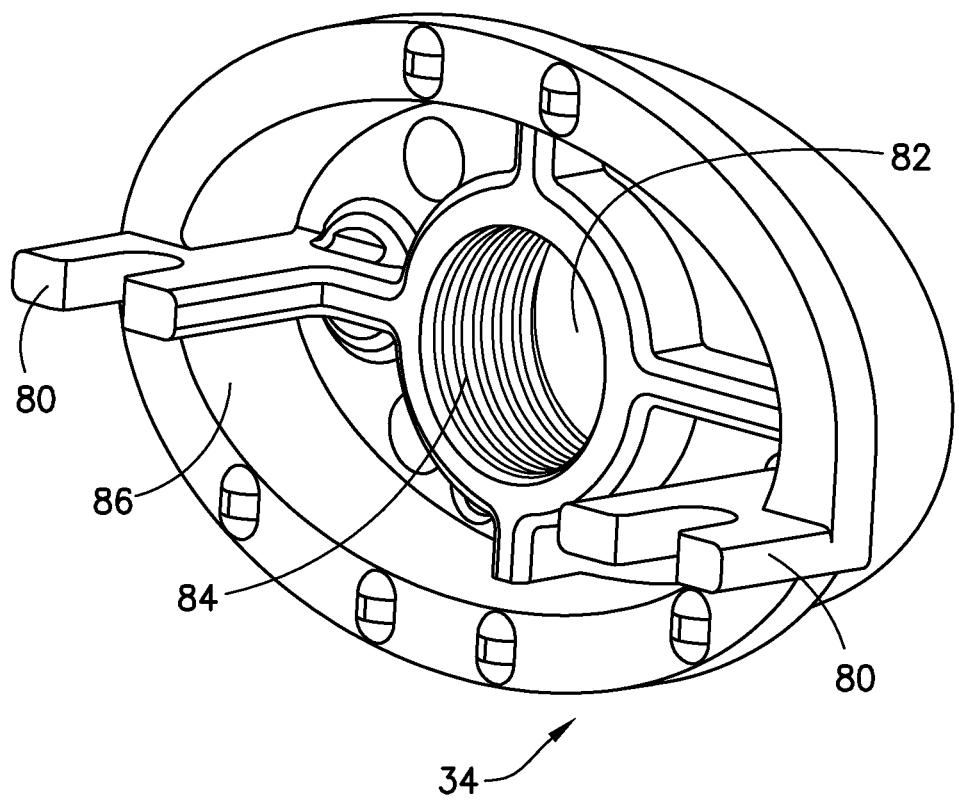
FIGS. 5A and 5B are, respectively, a rear perspective view and a front perspective view of a gear anchor constructed in accordance with an example embodiment.
Figure 5B:
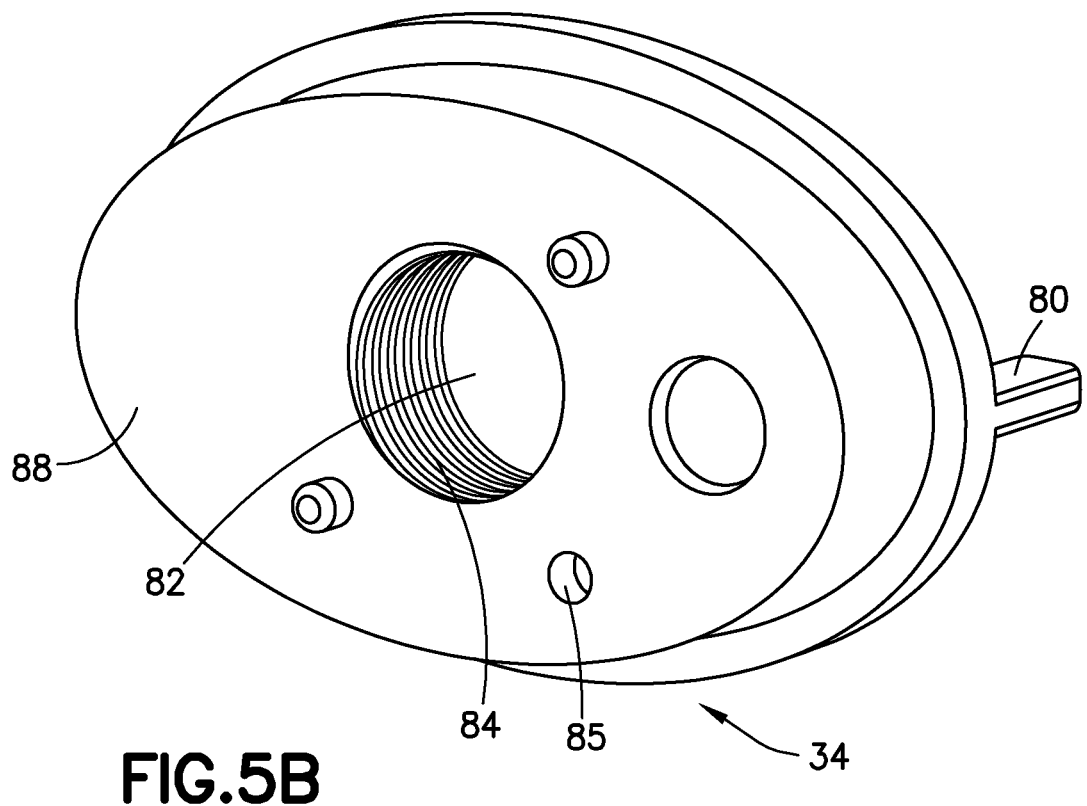

FIGS. 5A and 5B are, respectively, a rear perspective view and a front perspective view of a gear anchor 34 constructed in accordance with an example embodiment. The gear anchor 34 has protrusion(s) 80 to press fit it or otherwise engage pins or other components (not shown) provided on a reservoir mount (e.g., a wall on the baseplate, a mounting plate, a superstructure or other structure in the device housing 14). While a protrusion (e.g., a tab) 80 can hold the gear anchor 34 in place to react to forces from plunger movement and fluid pressure, other alternative example embodiments can be used to support the gear anchor 34 over a relatively large area to avoid localized deformations. The gear anchor 34 has an aperture 82 to receive a first portion of the nut 70. The aperture 82 has threads 84 that are configured to cooperate with the outer threads 72a of the sleeve screw 72. The number of threads 84 can be adjusted to balance torque and movement stability. The number of threads 84 can be added without negatively affecting length (i.e., only a small change in the drive nut geometry is needed). A recessed rear surface 86 is configured to rotatably receive a distal end of the nut 70. The gear anchor 34 has front surface 88 that can abut a plunger pusher 76 when the plunger driver assembly 30 is fully retracted and the reservoir is filled (e.g., as shown in FIG. 4D), but the gear anchor 34 is not required to abut the plunger depending on the dimensions of the reservoir 22 and the plunger driver assembly 30. The gear anchor 34 also has at least one aperture or through hole 85 for venting. As described below, the pusher 76 also has an opening(s) and/or clearances to allow venting as it moves axially in the reservoir 22.

Figure 6A:
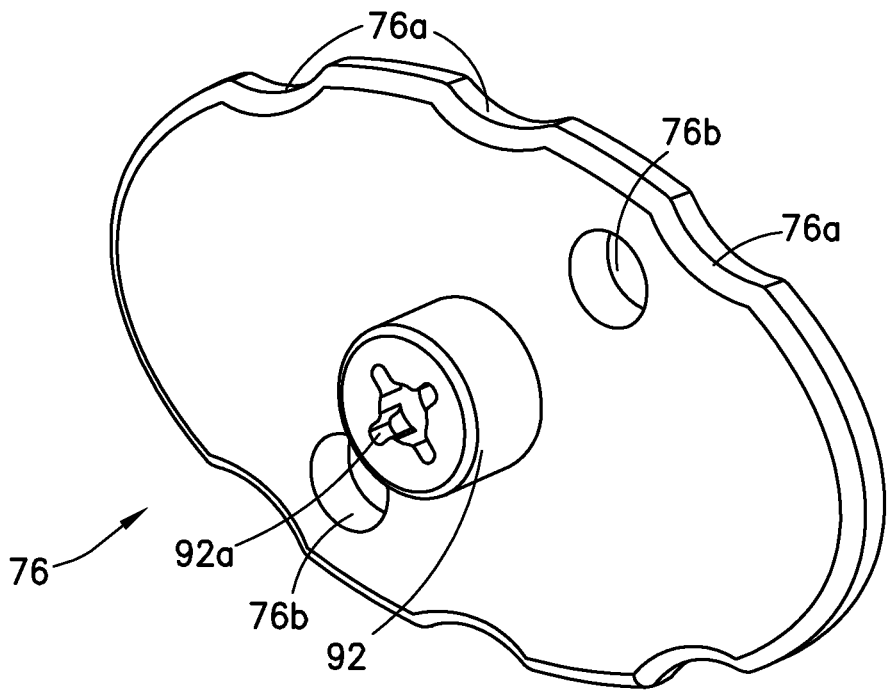
FIGS. 6A and 6B are, respectively, a front perspective view and a rear perspective view of a plunger pusher constructed in accordance with an example embodiment.
Figure 6B:
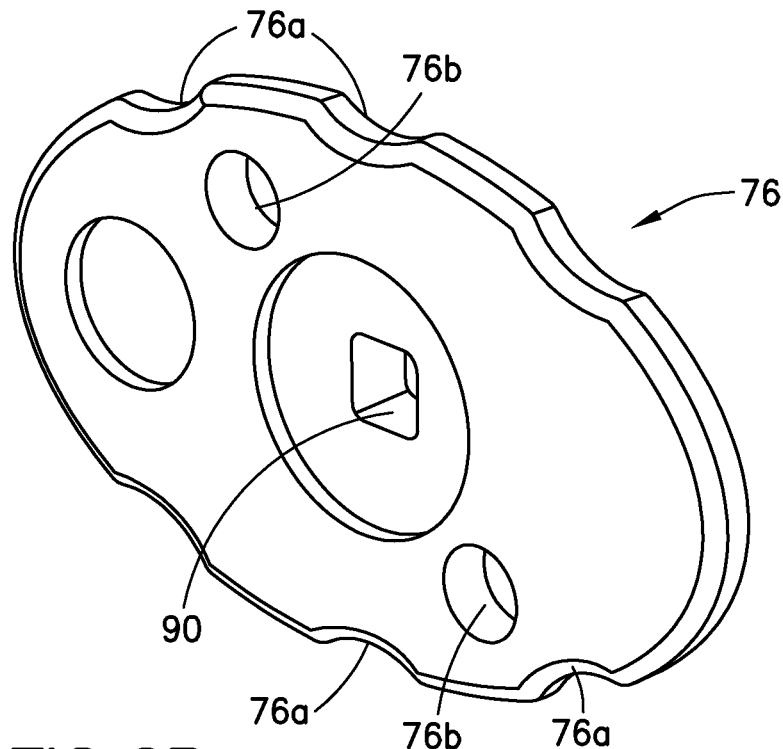

FIGS. 6A and 6B are, respectively, a front perspective view and a rear perspective view of a plunger pusher 76 constructed in accordance with an example embodiment. The plunger pusher 76 has a detent 90 on a rear surface thereof to receive a keying feature 74b on the center screw 74. An optional protrusion 92 on the front surface of the plunger pusher 76 can impact the rear surface of plunger 28. The pusher 76, together with or alternatively the cap 34 on the reservoir 22, is provided with feature(s) to allow air venting. For example, an air venting feature can be provided along at least a portion of the perimeter of the pusher 76 and be in the form of a scalloped edge comprising notches 76a. When notches 76a are provided on the perimeter of the pusher 76, these features can be arranged to minimize axial translation friction by biasing design and tolerances for edges around a few of these features 76a to be more proud of the remaining notch edges so as to make first contact with the internal reservoir barrel face to prevent rotation. The pusher 76 can also be provided with one or more through holes 76b in a plate-like portion of the pusher for venting.

Figure 7A:
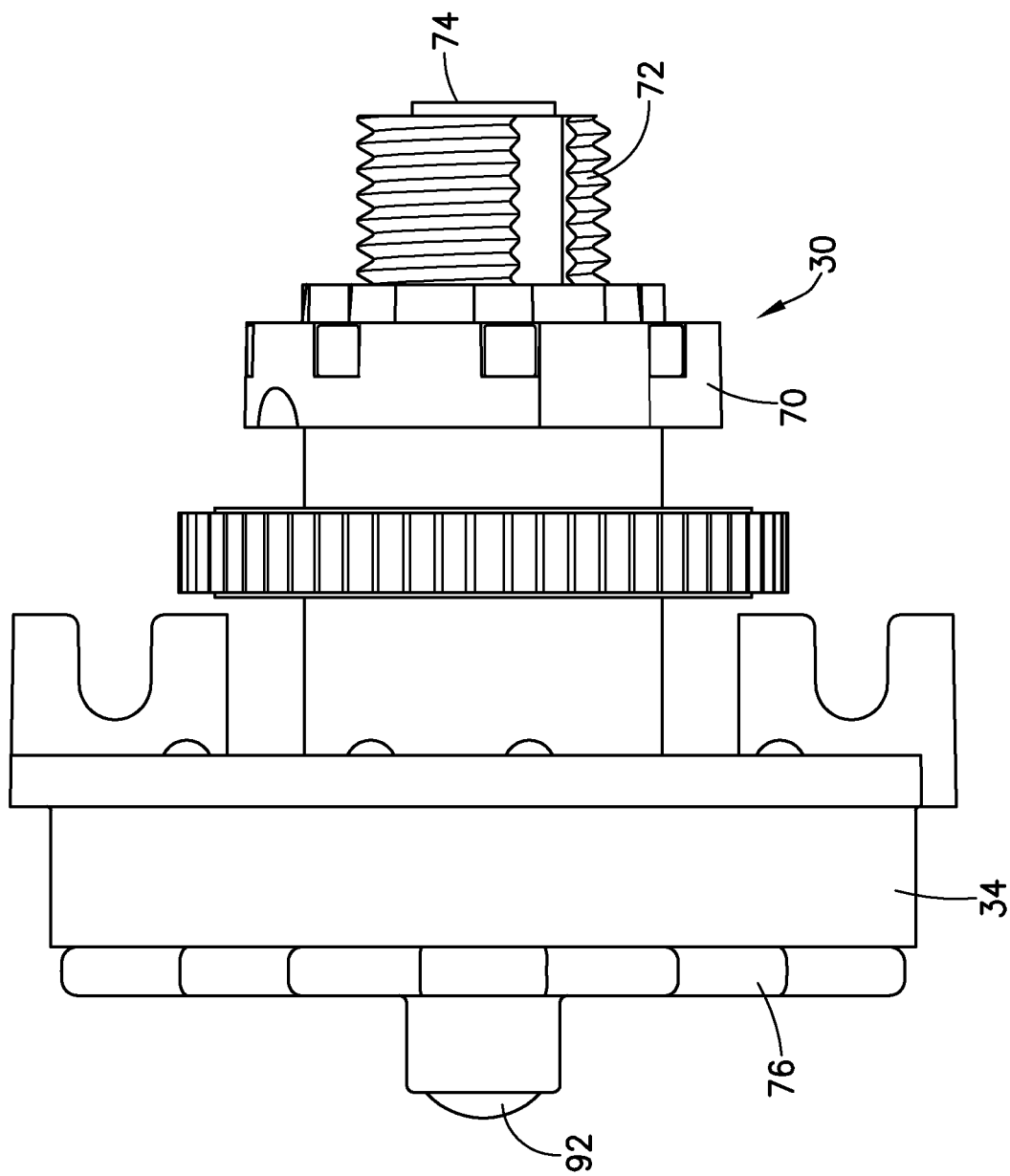
FIGS. 7A and 7B are, respectively, a side view of a plunger driver assembly in a retracted position relative to the gear anchor in accordance with an example embodiment, and an exploded view of the components shown in FIG. 7A.
Figure 7B:
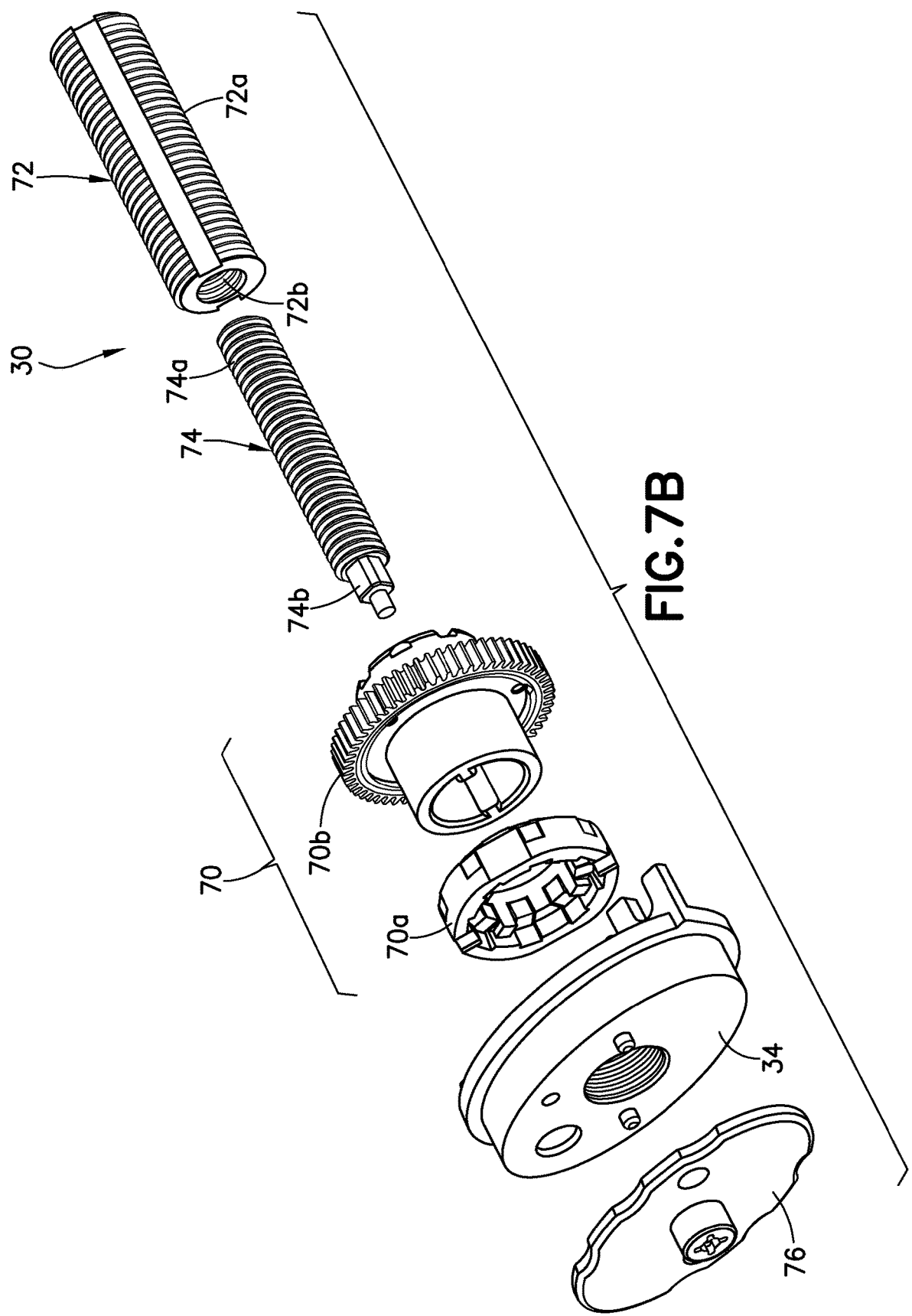

FIGS. 7A and 7B are, respectively, a side view of the plunger driver assembly 30 in a retracted position relative to the gear anchor 34 in accordance with an example embodiment, and an exploded view of the components shown in FIG. 7A. The plunger driver assembly 30 comprises the nut 70 having teeth 70b on a portion thereof that engages the gear train 32 and motor 18. A distal portion of the nut 70 is rotationally received in gear anchor 34. Inner threads 70c in the nut 70 engage outer threads 72a of the sleeve screw 72. Inner threads in 72b cavity of the sleeve screw engage outer threads 74a of the innermost or center screw 74. As described with respect to FIG. 9, the distal end of the center screw 74 is provided with a keying feature 74b that engages a detent 90 on the plunger pusher 76. As shown in FIG. 6A, the protrusion 92 can be provided with anti-rotation slots 92a. When assembled, the post on the distal end of the innermost screw 74 can extend into the detent 90, through the pusher 76 and slightly beyond its protrusion 92. The post on the distal end of the innermost screw 74 cooperates with the slots 92a during heat-staking of the innermost screw 74 relative to the pusher 76. The heat-staked end of the protrusion 92 is shown in FIG. 7A, for example. The nut 70 can be provided with an encoder 70a for indexing and accurate dose delivery and to provide feedback to the electrical module 50 to further protect against runaway or undesirable or inaccurate pump motor action and rotation of the drive nut 70.

Figure 8A:
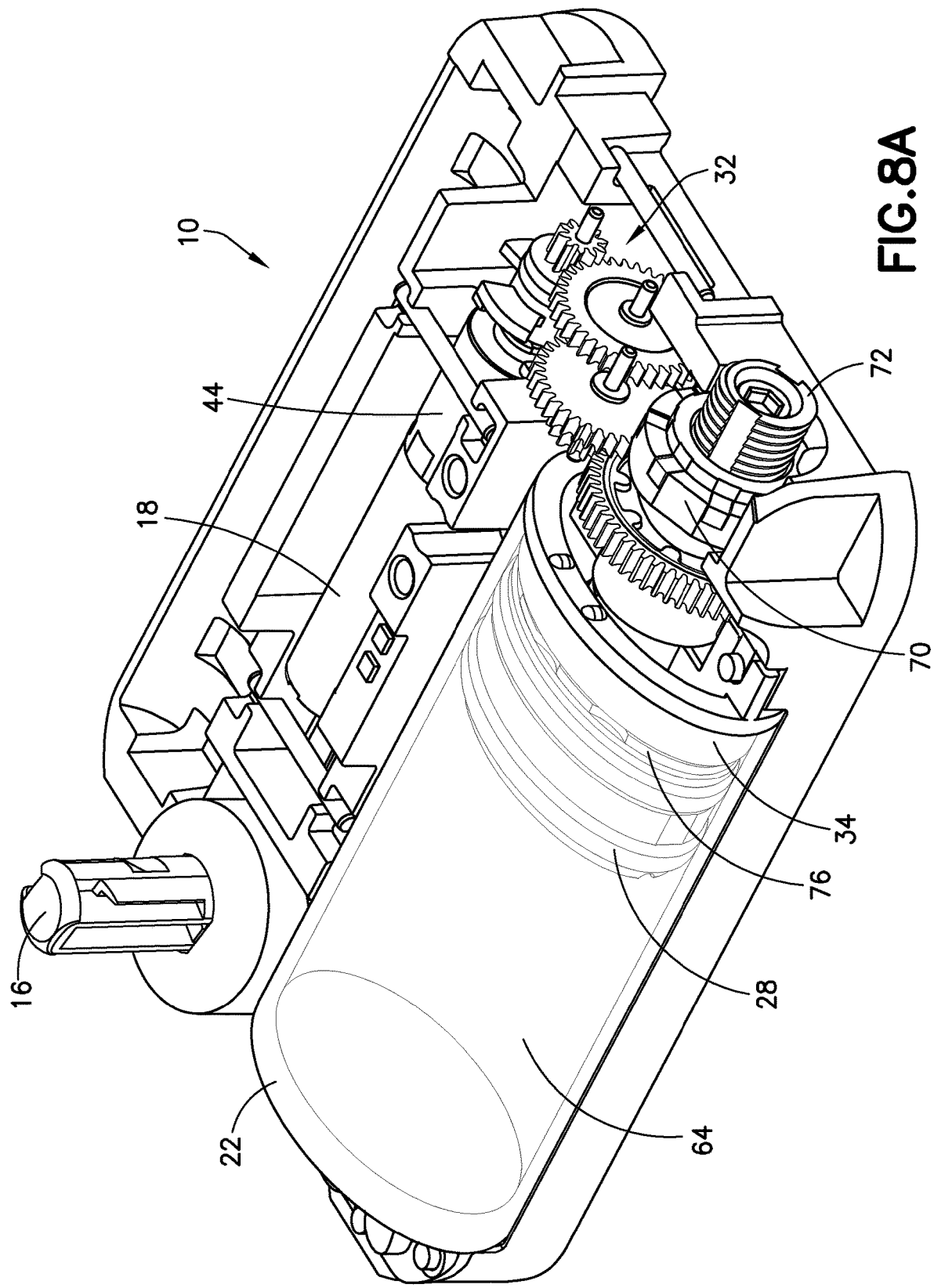
FIGS. 8A, 8B, 8C, 8D and 8E are perspective top views of a fluid delivery device with the cover removed and showing different stages of discharging fluid from a reservoir via a plunger drive assembly constructed in accordance with an example embodiment.

FIGS. 8A, 8B, 8C, 8D and 8E are perspective top views of a fluid delivery device with the cover removed and showing different stages of discharging fluid from a reservoir via a plunger drive assembly 30 constructed in accordance with an example embodiment. In FIG. 8A, the plunger drive assembly 30 is in a fully retracted position and the volume of the fluid filled chamber portion 64 of the reservoir 22 is maximized. The configuration of the double-acting, telescoping lead screw design of the plunger drive assembly 30 mounted behind the reservoir 22 is beneficial to maximize the available reservoir fluid volume while minimizing the reservoir's overall footprint on the baseplate 12. A rear portion of the sleeve screw 72 extends beyond the nut 70 when the plunger drive assembly 30 is in a full retracted position, but the overall length of the plunger drive assembly 30 when un-deployed and therefore the overall footprint of the reservoir 22 and plunger drive assembly 30 is minimized by the double-acting, telescoping lead screw design in accordance with the example embodiment.

Figure 8B:
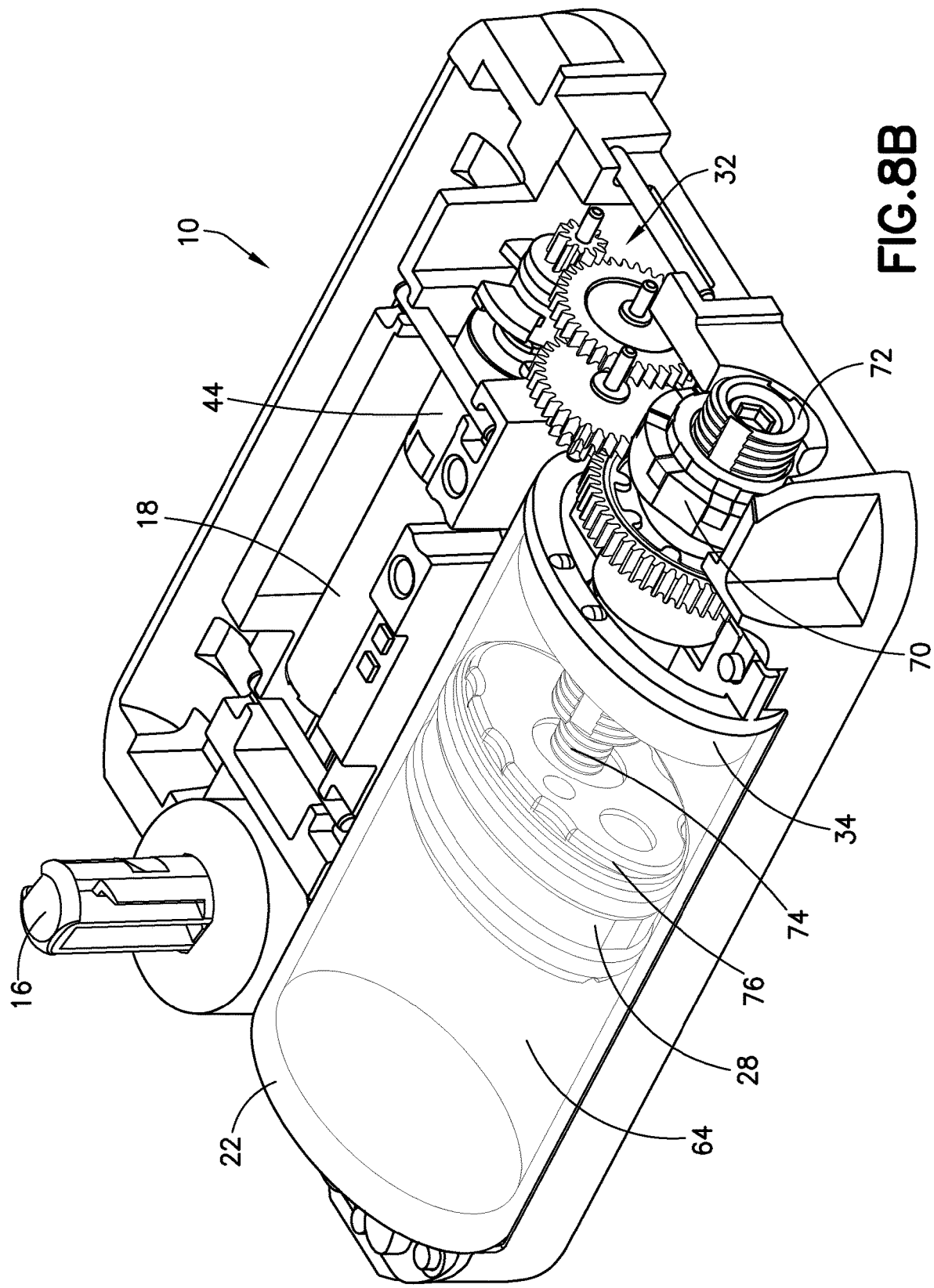
Figure 8C:
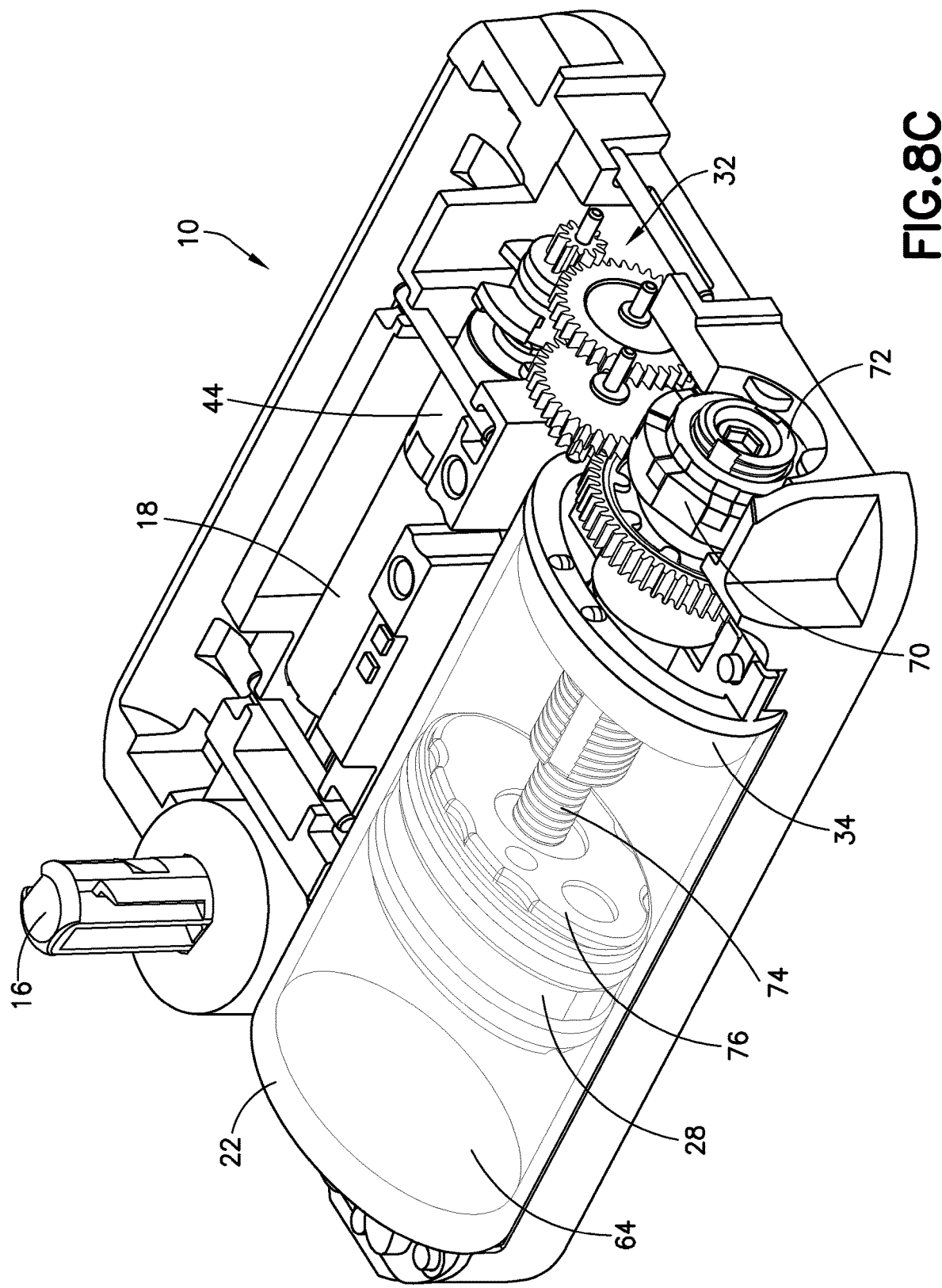
Figure 8D:
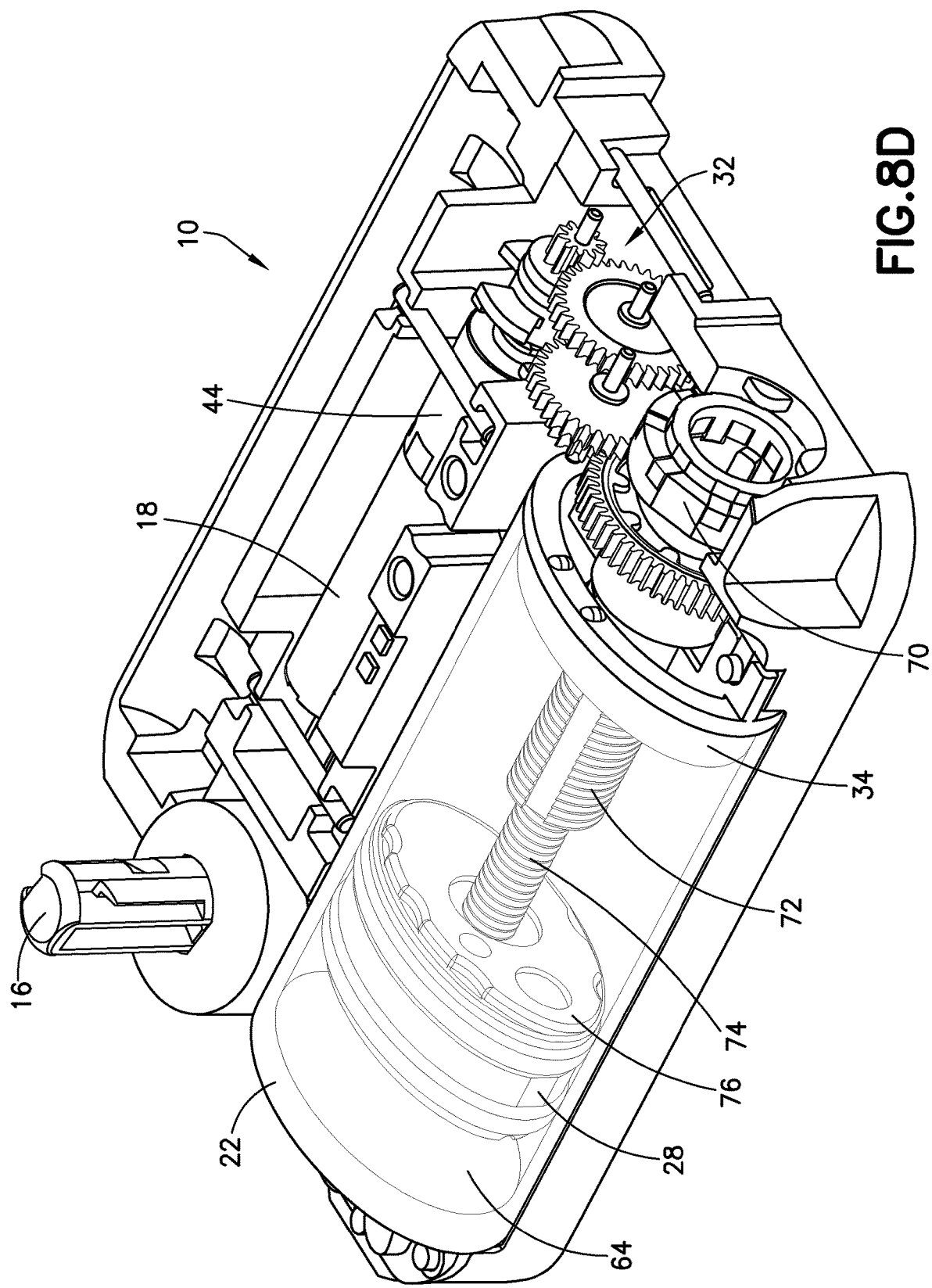
Figure 8E:
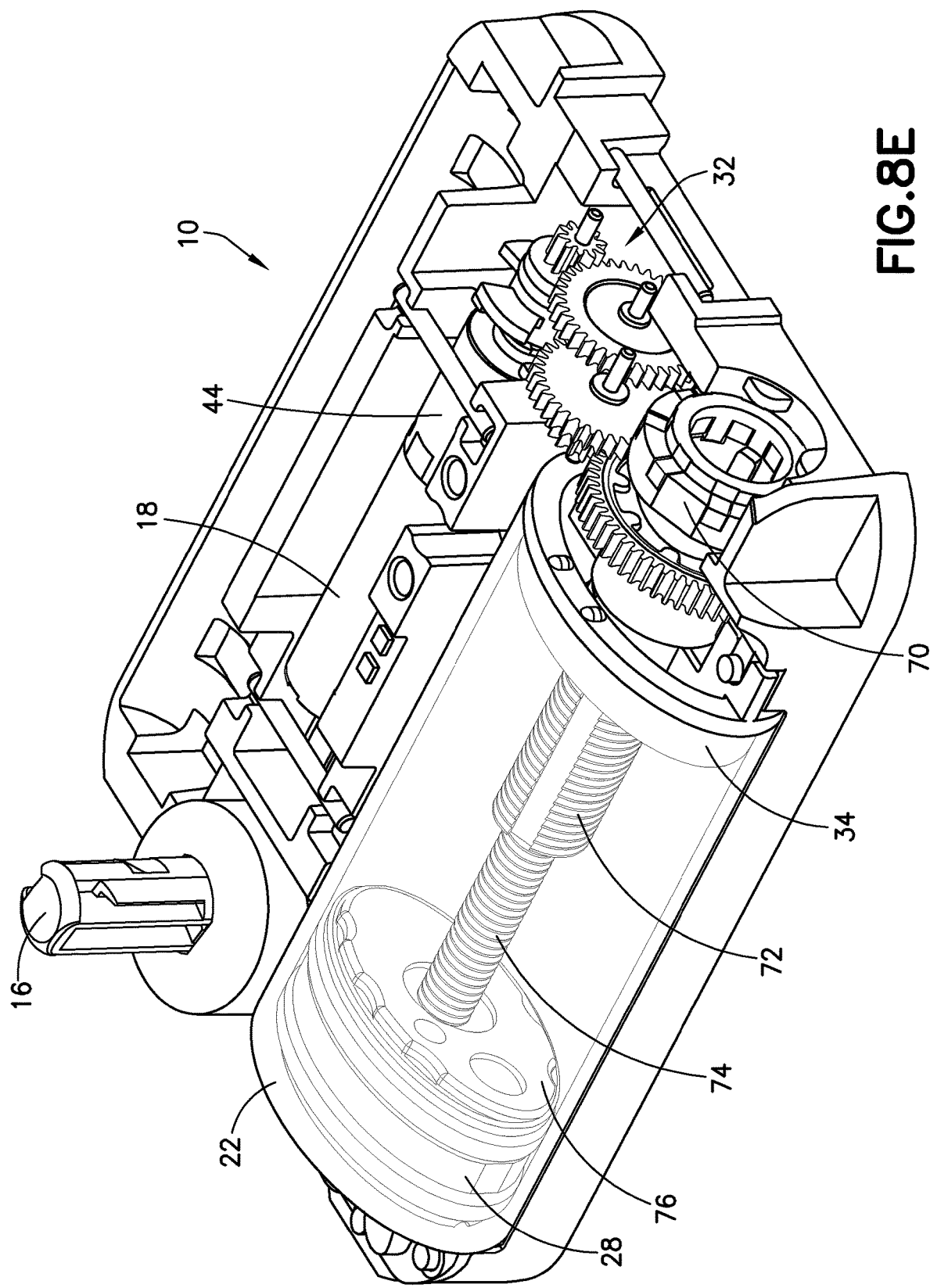

In FIG. 8B, the nut 70 is being rotated by the motor and gearbox 18 and the intermediate power transmission gear train 32 via engagement of its teeth 70b. The inner threads 70b of the nut and the aperture threads 84 of the gear anchor 34 cooperate with the outer threads 72a of the sleeve screw 72 to advance the sleeve screw 72 through the nut 70 and the gear anchor 34 and into the reservoir 22. Simultaneously, the rotation of the sleeve screw 72 causes non-rotational advancement of the center screw 74 which is keyed to the plunger pusher 76. As a result, the plunger 28 is advanced distally as plunger pusher 76 is advanced distally to abut the plunger 28. FIGS. 8C, 8D and 8E show further double-acting extension of the sleeve screw 72 and the center screw 74 at essentially equal lengths as the nut is rotated by the motor and gearbox 18 and the intermediate power transmission gear train 32.

With reference to FIGS. 6B and 9, the keying feature 74b on the center screw 74 and its corresponding detent 90 on the rear surface of the plunger pusher 76 provides an anti-rotation mechanism for the plunger pusher 76 relative to the reservoir 22 when the nut of the plunger drive assembly 30 is being rotated by the motor and gearbox 18 and the intermediate power transmission gear train 32. The center screw 74 uses a keyed feature to engage the plunger pusher 76. This keyed feature can either engage with a non-circular plunger pusher geometry, whereby rotation is prevented by geometry, or can be engaged with an intermediate structure that acts to prevent rotation in the operating syringe barrel-type reservoir 22. This keying feature 74b should be smaller than the outer thread of the same innermost screw (e.g., center screw 74) so that it may be assembled from the rear end of the assembly. For example, the distal end of the center screw 74 can be dimensioned and/or shaped to engage a corresponding dimensioned and/or shaped detent or indent 90 in the plunger pusher 76 that prevents any limited rotation imparted on the center screw 74 by the other components 70 and 72 from causing rotation of the plunger pusher 76 relative to the inner walls of the reservoir 22. This design can also rely on an elliptical syringe barrel-type reservoir 22 to contain the drug and provide anti-rotation functionality. The elliptical shape also has the added benefit of potentially saving device height.

The example embodiments described herein employ an elliptical syringe barrel-type reservoir 22 to contain the drug or fluid to be delivered. The elliptical syringe barrel-type reservoir 22 provides anti-rotation functionality and associated benefits. For example, anti-rotation provided by the intrinsic design of an elliptical syringe barrel-type reservoir 22 naturally prevents rotation of the barrel when a torque is applied. The elliptical shape also has the added benefit of potentially saving overall device height. It is, however, possible to employ a separate component to achieve the same anti-rotation. For example, the center screw 74 can be keyed to a detent or other feature 90 in the plunger pusher 76. Thus, even if the reservoir 22 is not elliptical (e.g., has a round cross-section), anti-rotation of the plunger driver assembly 30 relative to the inner walls of the reservoir 22 during axial translation is still achieved.

Reservoir 22 can be configured to be durable, that is, not removable but rather preinstalled within the fluid delivery device housing 14. The reservoir 22 can be similar in materials to a syringe barrel and associated stopper. The reservoir 22 can be prefilled and the plunger driver assembly 30 initially in a retracted position. Alternatively, the fluid delivery device housing 14 can be provided with a fill port and fluid path 26 from the fill port to the reservoir 22. The fill port can be configured for filling by a user with a syringe, or by using a filling station that fluidically couples to the fill port.

The example embodiments described herein employ a number of technical principle(s) such as: (a) screw wedge forces (e.g., opposing threads of the sleeve screw 72 and the center screw 74); (b) sliding coupling between the drive, the inner-threaded nut 70 and the sleeve screw 72 (e.g., the inner-threaded nut 70 and the sleeve screw 72 rotate together but the screw 72 translates axially outside of the nut 70); (c) an anti-rotation feature for the center screw 74 inside the barrel-type reservoir (e.g., either on the plunger pusher 76 or separate structure); (d) friction and gear power transmission with respect to the nut 70 and various threaded members; (e) syringe barrel-type drug container or reservoir 22 and aspect ratio adjustment to trade dosing resolution to drug type and use scenarios; and (f) optional flat cell-type batteries 20 for space saving.

It is to be understood that the example embodiments described herein can be subject to operative variations and alternative configurations. For example, different lead screw designs can be employed to change dosing resolution. Encoder(s) can be used to provide feedback of drive mechanism 30. Indexing drives can be employed to repeatably and fail-safe advance the plunger 28. Generally, non-circular syringe barrel cross-sections can be employed to optimize space utilization and tailor device size to best suit user comfort. Depending on the drug type and delivery rate, resolution needs, the syringe barrel-type reservoir 22 can be changed in aspect ratio, that is, a smaller ratio (wider cross-section, shorter barrel) can be employed to deliver a drug with low resolution, whereas a large aspect ratio can be employed to facilitate more precise dosing. In addition, the design is based on the basic screw-drive mechanism where lifting torque is a function of applied axial load (force or pressure), thread pitch, friction parameters, and diameter. In some cases, the equations can be further expanded to capture the full details of thread geometry such as flank and lead angle, and many other special parameters. ACME threads may be generally used to adjust the balance of lifting torque, power required, efficiency, and other functional parameters such as smoothness of operation and cost.

Figure 10A:
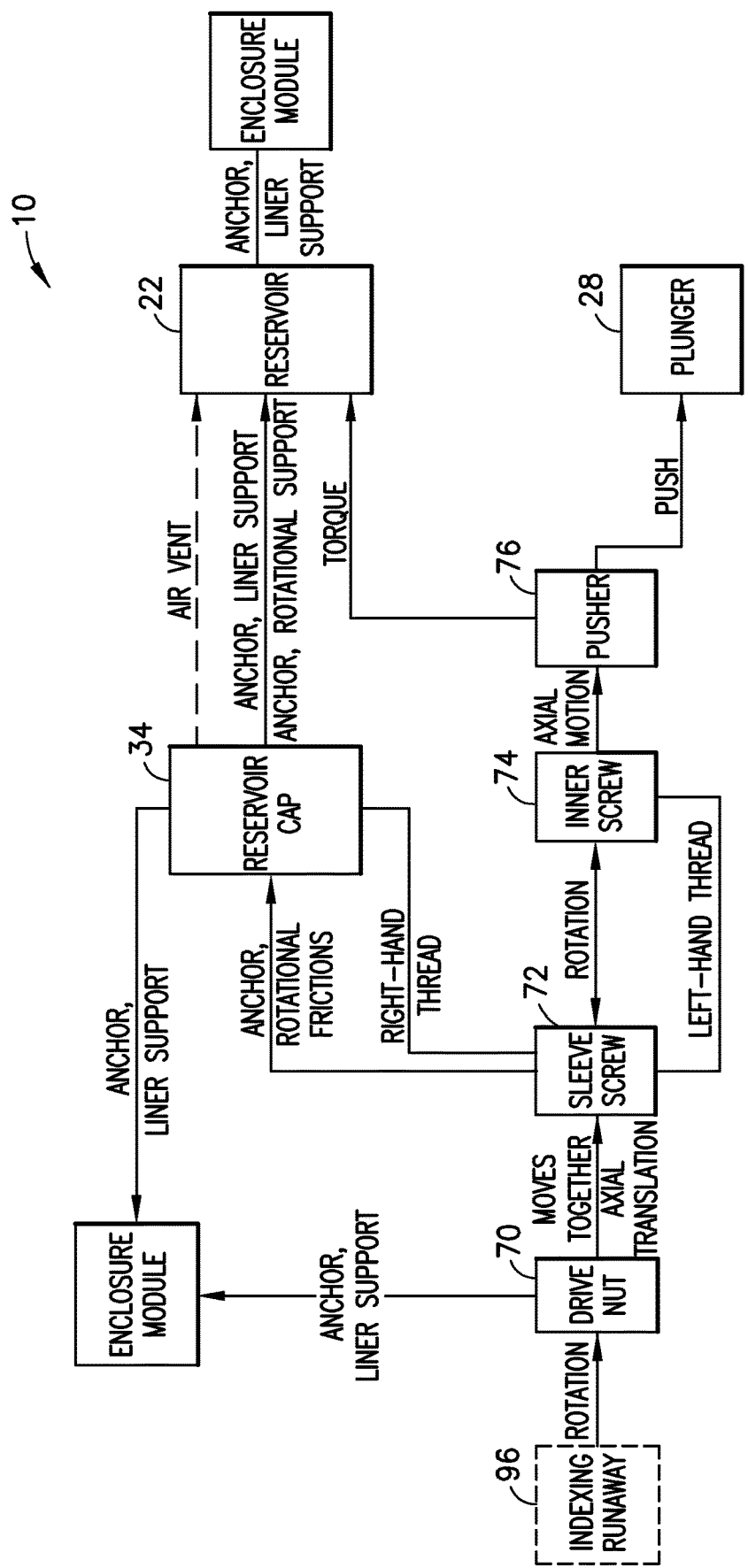
FIGS. 10A and 10B are respective block diagrams of a fluid delivery device having indexing and runaway prevention features and/or an encoder in accordance with example embodiments.
Figure 10B:
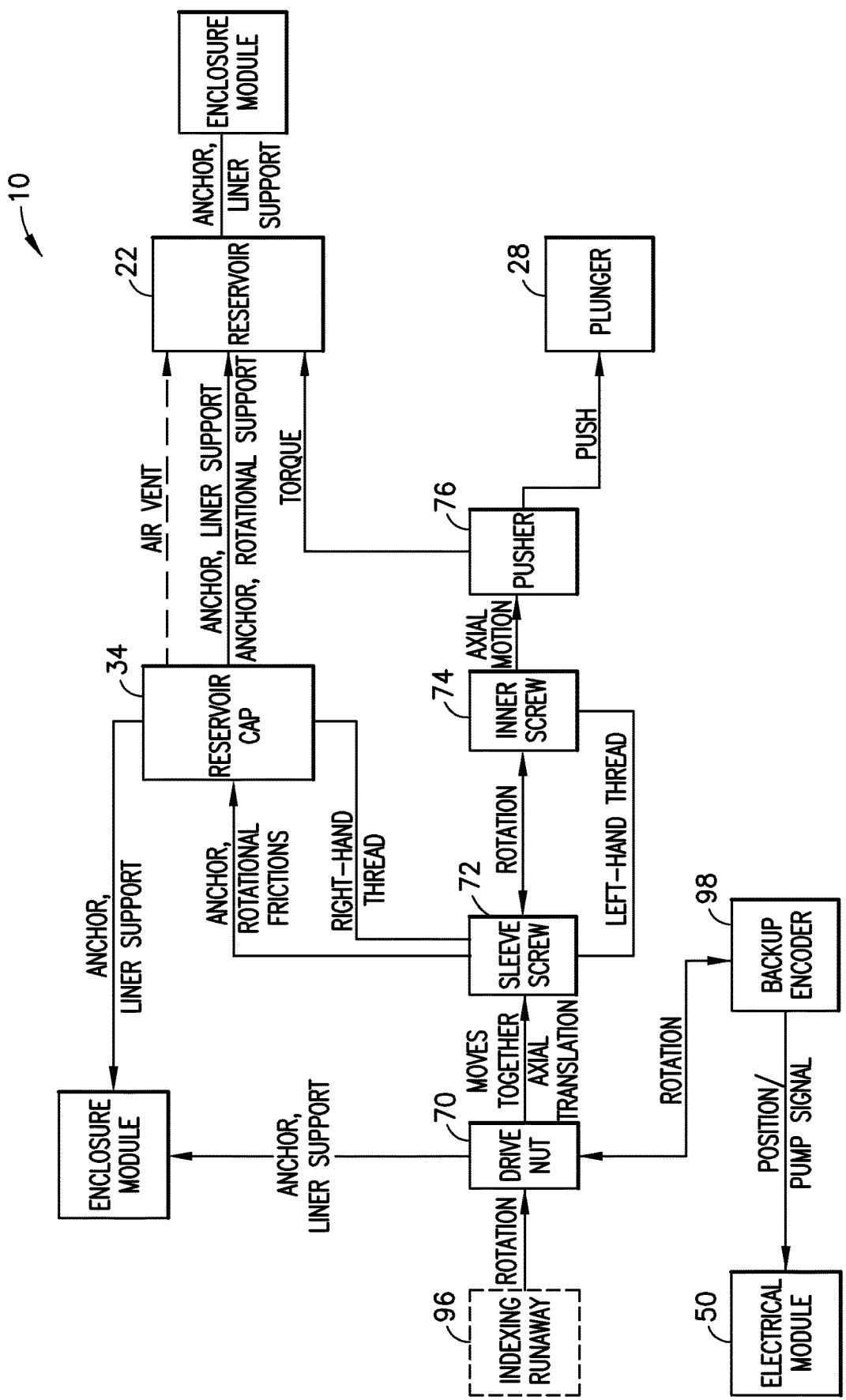

FIGS. 10A and 10B are respective block diagrams of a fluid delivery device 10 having an indexing and runaway prevention feature indicated generally at 96 and/or an encoder 98 in accordance with example embodiments. An indexer and runaway prevention device 96 can be provided with respect to the drive nut 70 to ensure controlled rotation of the nut 70 by the motor and thereby prevent runaway of the pump mechanism. As described above, the rotation of the drive nut 70 causes axial translation of the sleeve screw 72 which also causes axial translation of the center screw 74 due to the telescoping, simultaneously counter-rotation arrangement of the screw threads as described herein. The center screw 74 imparts axial motion to the pusher 76 of the plunger 28. The reservoir cap or gear anchor 34 provides linear and anchor support for the syringe barrel-type container or enclosure from friction by the sleeve screw. The gear anchor 34 can also provide an air vent, as well as anchor support, and linear and rotational support for the syringe barrel-type container or enclosure from axial movement and torque of the pusher due to engagement by the innermost screw 74. An encoder (e.g., a backup encoder) 98 can also be connected to the drive nut 70 and provide feedback to the electrical module 50 to further protect against runaway or undesirable or inaccurate pump motor action and rotation of the drive nut 70 (e.g., the electrical module can power down the motor if a runaway condition is sensed by the encoder 98).

The example embodiments described herein and their equivalent variations provide technical solutions to a number of technical problems with existing fluid delivery devices and particularly patch-type or wearable fluid delivery devices. For example, no existing wearable, disposable patch pump exists with the nesting, telescoping, simultaneously counter-rotating screw technology described herein. Use of the example embodiments enables the use of a standard syringe barrel-type container as the reservoir 22, thus simplifying drug compatibility while bringing significant space savings to the mechanical drive mechanism that resides fully outside of the syringe barrel and behind the moving plunger 28. A large volume reservoir can be employed that exceeds existing device functionality on the market.

Further, the compact design afforded by the example embodiments allows additional flexibility in reservoir cross-section design, thus enabling fluid delivery device designers to have additional design control that may benefit dosing accuracy by, for instance, slightly reducing the cross-section (and extending the length), thus requiring more travel to dispense a minimal fluid dose. This increased travel corresponds to greater rotation of the rotating drive gear which, in turn, means that the drive motion can be more precise.

A further technical solution provided by the example embodiments is the use of an elliptical cross-section syringe barrel-type container for the reservoir 22. The rotating screw (e.g., screw 72) that pushes on the barrel (e.g., via the nut 70 and gear anchor 34 configuration) will naturally apply a rotational movement to the barrel 22. Thus, a physical feature is beneficial to prevent rotation. An elliptical syringe cross-section achieves this requirement, as it does not allow rotation as would a circular cross-section. It is to be understood that the cross-sectional shape of the reservoir and plunger can be of any non-circular shape. While an elliptical is cross-sectional shape geometrically easier to implement in order to facilitate sealing and balancing forces, other shapes may enable better packaging. Additional methods to prevent rotation can be implemented depending on how the filling process is implemented. For example, if a variable fill is desired with a syringe 36 (e.g., operated by the patient), then the plunger 28 can be assembled bottomed out and pushed to an initial position by the fill volume. With an anti-rotation feature attached to the innermost screw (e.g., center screw 74), the same screw set can advance and then properly engage the plunger by having pre-aligned engagement features.

The configuration of the plunger driver assembly 30 components with respect to the reservoir 22 and the plunger 28 realizes a number of other advantages. For example, having a plunger drive assembly 30 mounted at a proximal end of the reservoir 22 and having a nested configuration that does not extend into the reservoir until the nut 70 is rotated optimizes use of the reservoir chamber for fluid delivery instead of having to accommodate pre-delivery plunger driver components. In addition, the overall length of the reservoir can be substantially the same as the length of the housing, with the addition of a small amount of headspace to accommodate the gear train 34 connection to the drive gear teeth 70b of the nut 70 and nominal length of the sleeve screw 72 extending from the nut in the fully retracted position. Thus, the overall footprint of the pump mechanism is minimized as well as the longitudinal axis dimension of the fluid delivery device housing 14. The use of the plunger 28 and plunger drive assembly 30 design also minimizes contact of the pump mechanism with the fluid being delivered to ensure biocompatibility between the fluid and the fluid delivery housing. The example embodiments described herein employ nested telescoping screws of appropriate size and thread configuration to achieve a controlled movement of a syringe-barrel-type reservoir plunger 28. Screw-thread technology is well-defined and understood, and is capable of repeatable, powerful motion. When driven with an appropriate resolution-controlled motion by the motor 18, the nested screws (e.g., 72 and 74) can provide accurate movement under virtually all environmental conditions. Further, the drive mechanism (e.g., the plunger driver assembly 30) the does not affect the basic volume of the fluid chamber 64 where the drug resides, thus having no impact on any compatibility issues.

Although various persons, including, but not limited to, a patient or a healthcare professional, can operate or use illustrative embodiments of the present disclosure, for brevity an operator or user will be referred to as a "user" hereinafter.

Although various fluids can be employed in illustrative embodiments of the present disclosure, for brevity the liquid in an injection device will be referred to as "fluid" hereinafter.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A fluid delivery device comprising:
a reservoir comprising an outlet port at a distal end, and a plunger movable along a longitudinal axis of the reservoir, the plunger configured to provide a seal with respect to inner walls of the reservoir to prevent fluid provided in a fluid chamber defined on a first side of the plunger and comprising the outlet port from leaking into a portion of the reservoir defined by a second side of the plunger; and
a plunger driver assembly mounted at a proximal end of the reservoir and comprising telescoping, simultaneously counter-rotating screws having similar pitch and lead parameters that, when a threaded nut is rotated, move from a nested configuration that does not extend into the reservoir to an extended configuration that extends into the reservoir at a rate of double the individual pitch and lead parameters of the respective screws.

2. The fluid delivery device of claim 1, wherein the screws comprise a sleeve screw and a center screw each having opposite handed outer threads, the outer threads of the center screw being right hand threads if the outer threads of the sleeve screws are left-hand threads, and the outer threads of the center screw being left-hand threads if the outer threads of the sleeve screw are right-hand threads.

3. The fluid delivery device of claim 2, wherein inner threads of the sleeve screw and the outer threads of the sleeve screw are opposite handed threads.

4. The fluid delivery device of claim 2, wherein the threaded nut has an aperture with inner threads that cooperate with the outer threads on the sleeve screw to advance the sleeve screw into the reservoir when the threaded nut is rotated.

5. The fluid delivery device of claim 4, wherein the reservoir further comprises a gear anchor mounted to its proximal end, the gear anchor comprising an aperture dimensioned to receive a distal end of the sleeve screw and allow the sleeve screw and the center screw to extend into the reservoir when the threaded nut is rotated.

6. The fluid delivery device of claim 5, wherein the gear anchor comprises a through hole for venting.

7. The fluid delivery device of claim 2, wherein the plunger driver assembly further comprises a plunger pusher coupled to a distal end of the center screw.

8. The fluid delivery device of claim 7, wherein the plunger pusher is configured to detachably abut the plunger and push the plunger axially toward the distal end of the reservoir when the plunger driver assembly is controlled to deploy the counter-rotating screws to discharge a designated amount of fluid from the fluid chamber in the reservoir through displacement of the plunger.

9. The fluid delivery device of claim 7, wherein the plunger pusher comprises at least one through hole for venting.

10. The fluid delivery device of claim 7, wherein the plunger pusher comprises indents along at least a portion of its perimeter for venting.

11. The fluid delivery device of claim 2, wherein the center screw is connected to a plunger pusher coupled to a distal end of the center screw and constrained from rotation by an anti-rotation mechanism configured as the reservoir and the plunger pusher having a non-circular cross-section to prevent rotation of the plunger pusher within the reservoir when the sleeve screw is rotated.

12. The fluid delivery device of claim 2, wherein the center screw is connected to a plunger pusher coupled to a distal end of the center screw, and the plunger driver assembly further comprises an anti-rotation mechanism that comprises a detent on a proximal side of the plunger pusher dimensioned to cooperate with a distal end of the center screw to prevent the plunger pusher from rotating relative to the inner walls of the reservoir when the sleeve screw is rotated.

13. The fluid delivery device of claim 12, wherein the distal end of the center screw is dimensioned and/or shaped to be pressure fit into a correspondingly dimensioned and/or shaped detent.

14. The fluid delivery device of claim 12, wherein the detent comprises a through hole to a distal side of the plunger pusher, and the distal end of the center screw extends through the through hole.

15. The fluid delivery device of claim 14, wherein the distal end of the center screw is heat staked at the distal side of the plunger pusher at the through hole.

16. The fluid delivery device of claim 15, wherein the through hole comprises anti-rotation slots.

17. The fluid delivery device of claim 14, wherein the plunger pusher comprises a protrusion on its distal side and the through hole extends through the protrusion.

18. The fluid delivery device of claim 1, wherein the reservoir comprises an inlet port connected via an inlet fluid path to a fill port provided in the fluid delivery device to couple with a filling apparatus, and the plunger is configured to be displaced toward the proximal end of the reservoir as fluid is introduced into the fluid chamber from the inlet port, the plunger driver assembly being configured in its nested configuration during filling.

19. The fluid delivery device of claim 1, wherein the reservoir is a syringe barrel-type container.

20. The fluid delivery device of claim 1, wherein the reservoir and the plunger have a cross-sectional shape chosen from a non-circular shape, and an elliptical cross-section.

21. The fluid delivery device of claim 1, wherein the respective screws have equal pitch.

22. The fluid delivery device of claim 1, further comprising an encoder provided relative to the plunger driver assembly to generate feedback data related to operation of the plunger driver assembly.

* * * * *